(12) United States Patent
Cho et al.

(10) Patent No.: US 9,987,631 B2
(45) Date of Patent: Jun. 5, 2018

(54) SELECTIVE PARTICLE CAPTURE AND COLLECTION DEVICE

(75) Inventors: Young-Ho Cho, Daejeon (KR); Il Doh, Daejeon (KR); Hwan-Il Yoo, Seoul (KR)

(73) Assignee: NEXVIVO CO., LTD., Daejeon (KR)

( * ) Notice: Subject to any disclaimer, the term of this patent is extended or adjusted under 35 U.S.C. 154(b) by 94 days.

(21) Appl. No.: 13/583,097

(22) PCT Filed: Aug. 5, 2010

(86) PCT No.: PCT/KR2010/005126
§ 371 (c)(1),
(2), (4) Date: Sep. 6, 2012

(87) PCT Pub. No.: WO2011/111908
PCT Pub. Date: Sep. 15, 2011

(65) Prior Publication Data
US 2012/0329141 A1    Dec. 27, 2012

(30) Foreign Application Priority Data

Mar. 10, 2010  (KR) .................. 10-2010-0021255

(51) Int. Cl.
| | |
|---|---|
| *B01L 3/00* | (2006.01) |
| *C12M 1/34* | (2006.01) |
| *G01N 33/487* | (2006.01) |
| *G01N 1/40* | (2006.01) |
| *G01N 15/02* | (2006.01) |
| *G01N 15/00* | (2006.01) |

(52) U.S. Cl.
CPC ... *B01L 3/502746* (2013.01); *B01L 3/502753* (2013.01); *G01N 1/4077* (2013.01); *G01N 15/0272* (2013.01); *B01L 2200/0668* (2013.01); *B01L 2300/0816* (2013.01); *B01L 2300/0877* (2013.01); *B01L 2400/086* (2013.01); *G01N 2015/0053* (2013.01)

(58) Field of Classification Search
None
See application file for complete search history.

(56) References Cited

U.S. PATENT DOCUMENTS

| | | |
|---|---|---|
| 6,632,652 B1 | 10/2003 | Austin et al. |
| 2005/0207940 A1* | 9/2005 | Butler et al. ................ 422/73 |
| 2007/0172903 A1* | 7/2007 | Toner et al. ............. 435/7.23 |
| 2011/0045994 A1* | 2/2011 | Voldman ......... B01L 3/502761 |
| | | 506/7 |

FOREIGN PATENT DOCUMENTS

| | | |
|---|---|---|
| JP | 4152885 | 5/1992 |
| KR | 100899138 | 5/2009 |
| KR | 20090089650 | 8/2009 |

* cited by examiner

*Primary Examiner* — Jill A Warden
*Assistant Examiner* — Julie L Tavares
(74) *Attorney, Agent, or Firm* — Fildes & Outland, P.C.

(57) ABSTRACT

A particle processing device includes a chamber and at least one capturing structure. The chamber is connected to a first port and a second port to provide a space between the first and second ports for flowing of a fluid having a particle. The capturing structure is provided in the chamber to form a fluidic channel, wherein the fluidic channel has a first opening and a second opening and a capturing region is formed between the first and second openings such that the capturing region has a changeable sectional shape for capturing the particle in the fluid flowing from the first port to the second port.

15 Claims, 26 Drawing Sheets

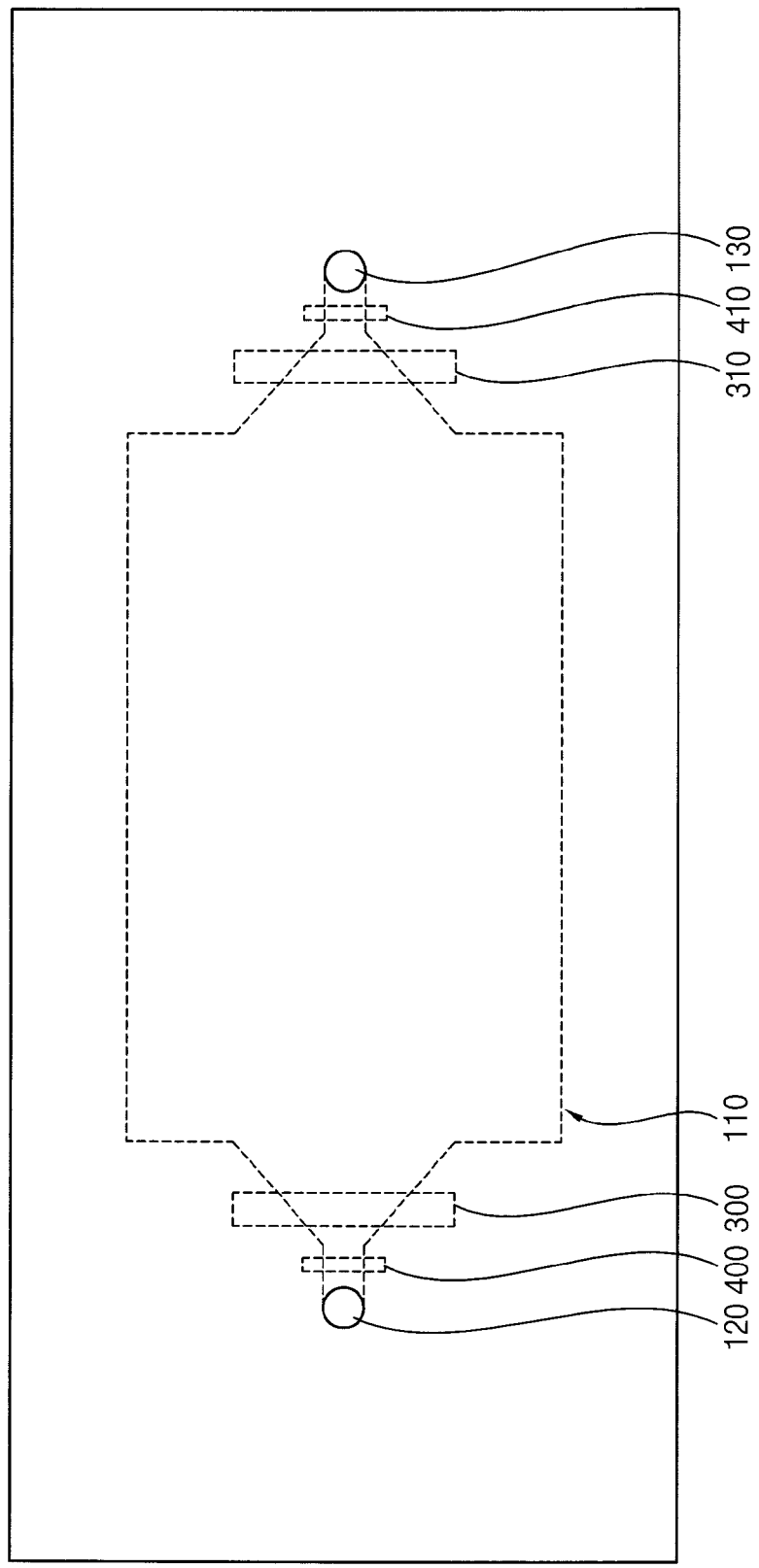

FIG. 16B
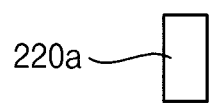
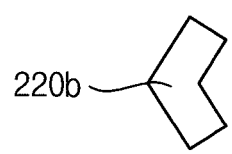
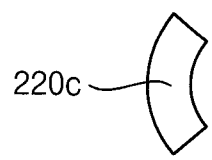

SELECTIVE PARTICLE CAPTURE AND COLLECTION DEVICE

CLAIM OF PRIORITY

This application claims priority under 35 USC § 119 to Korean Patent Application No. 2010-0021255, filed on Mar. 10, 2010 in the Korean Intellectual Property Office (KIPO), the contents of which are herein incorporated by reference in their entirety.

BACKGROUND

1. Field

Example embodiments relate to a particle processing device. More particularly, example embodiments relate to a device for selectively capturing a particle in a fluid and collecting the captured particle.

2. Description of the Related Art

Generally, technologies of detecting and capturing a micro-particle in a fluid may be performing biochemical surface processes to increase the adhesive adhesive strength with the particle, or using a physical characteristic of the particle.

However, in case of detecting the particle based on only the biochemical or physical characteristic of the particle, there are many problems that can occur, such as inaccurate detections of undesired particles, losses of the target particles and changes in biochemical characteristics of the target particles in a detection process, etc.

SUMMARY

Example embodiments provide a device for separating and detecting particles by using multiple characteristics of the particle.

Example embodiments provide a device for capturing and collecting particles by using bidirectional flow in a fluidic chamber.

According to example embodiments, there is provided a particle processing device. The device includes a chamber and at least one capturing structure. The chamber is connected to a first port and a second port to provide a space between the first and second ports for flowing of a fluid having a particle. The capturing structure is provided in the chamber to form a fluidic channel, wherein the fluidic channel has a first opening and a second opening and a capturing region is formed between the first and second openings such that the capturing region has a changeable sectional shape for capturing the particle in the fluid flowing from the first port to the second port.

In example embodiments, the first opening may have a first size and the second opening may have a second size smaller than the first size. The second size of the second opening may be smaller than the minimum size of the particle that is deformed under a local pressure due to the physical characteristics of the particle such as deformability or stiffness.

In example embodiments, the capturing structure may include a pair of channel patterns that are formed between opposing upper and lower sidewalls of the chamber to define the fluidic channel.

In this case, the width of at least one of the channel patterns may be gradually changed along the extending direction thereof to define the size of at least one of the first and second openings. At least one of the channel patterns may be deformed by an external force to change the opening size of the fluidic channel. At least one of the channel patterns may be deformed by an external force to be generated or removed between the upper and lower sidewalls. Any one of the sidewalls of the chamber may be deformed by an external force such that the deformed sidewall and the channel patterns form the fluidic channel.

In example embodiments, an inner surface of the fluidic channel of the capturing structure may be partially or entirely deformed to form the capturing region.

In example embodiments, the device may further include at least one auxiliary structure provided adjacent to the capturing structure in the chamber to selectively allow or prevent entering of specific particles into the fluidic channel according to the moving direction of the particles between the first port and the second port.

In this case, the auxiliary structure may be arranged adjacent to the second opening of the capturing structure.

The auxiliary structure may include at least one auxiliary structure pattern that is formed between opposing upper and lower sidewalls of the chamber. The auxiliary structure pattern may be spaced apart from the capturing structure by a first distance, and the first distance may be smaller than the minimum diameter of the particle that is deformed under a local pressure due to the physical characteristics of the particle such as deformability or stiffness. The auxiliary structure pattern may be deformed by an external force or fluid flow to change the distance between the capturing structure and the auxiliary structure. The auxiliary structure pattern may be deformed by an external force to be generated or removed.

In example embodiments, a biochemical material layer may be formed on at least one of the capturing structure and the auxiliary structure or surface treatment may be performed on the at least one of the capturing structure and the auxiliary structure to change surface characteristics, in order to increase or decrease the adhesive strench with the particle.

According to example embodiments, there is provided a particle processing device. The device includes a first input/output portion, a second input/output portion, a chamber and at least one channel array. The first input/output portion has a first port through which a fluid having a particle flows. The second input/output portion has a second port through which the fluid flows. The chamber is connected to the first port and the second port to provide a space between the first and second ports for flowing of the fluid. The channel array is provided in the chamber and includes a plurality of unit structures of a capturing structure and an auxiliary structure, wherein the capturing structure forms a fluidic channel having a capturing region for capturing the particle in the fluid flowing from the first port to the second port, and the auxiliary structure is provided adjacent to the capturing strcutrue to prevent undesired particles from flowing into the fluidic channel when a fluid flows from the second port to the first port.

In example embodiments, the device may further include at least one auxiliary path that is formed adjacent to the channel array to control the fluid flow in the chamber.

In example embodiments, the capturing structures of the channel array may include channel patterns that are spaced apart from one another by different distances. The capturing structures of the channel array may include channel patterns having different shapes.

In example embodiments, the auxiliary structures of the channel array may include auxiliary structure patterns that are spaced apart from one another by different distances. The auxiliary structures of the channel array may include auxiliary structure patterns having different shapes.

In example embodiments, the fluidic channels of the unit structures may be arranged parallel with the flow direction of the fluid or inclined at a predetermined angle with respect to the flow direction of the fluid.

In example embodiments, the capturing structures of the channel array may include the fluidic channels with 2-dimensional arrangement.

In example embodiments, the channel array may include a first channel array and a second channel array. In this case, the first channel array may include first unit structures that are arranged inclined at a first angle with respect to the flow direction of the fluid and the second channel array may include second unit structures that are arranged inclined at a second angle different from the first angle with respect to the flow direction of the fluid.

In example embodiments, the first input/output portion may include a fluid transfer element that is connected to the first port to perform at least one function of fluid-supplying, pressure-supplying, releasing and draining.

In example embodiments, the first input/output portion may supply buffer fluids together with the fluid to conroll the flow direction of the fluid.

In example embodiments, the first input/output portion may further include a guide structure between the first port and the chamber to controll the flow direction of the fluid.

In example embodiments, at least one of the first input/output portion and the second input/output portion may further include a filter for preventing undesired particles from flowing into the chamber. The filter may include a first filter arranged adjacent the first port and the first filter may have an opening greater than the first opening of the fluidic channel. The filter may include a second filter arranged adjacent the second port and the second filter may have an opening smaller than the second opening of the fluidic channel.

In example embodiments, the device may further include a counter that is arranged adjacent to at least one of the first port, the second port, the unit structure and the channel array to detect the number of the particles.

In example embodiments, a biochemical material layer may be formed on at least one of the capturing structure and the auxiliary structure or surface treatment may be performed on the at least one of the capturing structure and the auxiliary structure to change surface characteristics, in order to increase or decrease the adhesive strench with the particle.

According to example embodiments, the particle processing device may include at least one capturing structure formed in the fluidic chamber or a channel array including the capturing structure. The particle processing device may efficiently capture and collect particles by using bidirectional flow in the chamber and conduct real time quantitative analysis with a counter.

BRIEF DESCRIPTION OF THE DRAWINGS

Example embodiments will be more clearly understood from the following detailed description taken in conjunction with the accompanying drawings. FIGS. 1 to 25 represent non-limiting, example embodiments as described herein.

FIG. 1 is a plan view illustrating a particle processing device in accordance with an example embodiment.

FIG. 2 is a plan view illustrating first and second input/output portions of the particle processing device in FIG. 1.

FIG. 4 is a plan view illustrating the chamber of the particle processing device in FIG. 1.

FIG. 5 is an enlarged perspective view illustrating the "A" portion in FIG. 4.

FIG. 6 is a cross-sectional view taken along the VI-VI' line in FIG. 4.

FIG. 7 is a plan view illustrating the unit structure of the particle processing device in accordance with an example embodiment.

FIG. 12 is a cross-sectional view illustrating a modified chamber.

FIG. 14 is a plan view illustrating a modified particle processing device.

FIGS. 16A and 16B are plan views illustrating various arrangements of auxiliary structures of channel array.

FIG. 17 is a plan view illustrating modified channel arrays in a chamber.

FIGS. 20 to 25 are views illustrating a particle processing method in accordance with an example embodiment.

DESCRIPTION OF EMBODIMENTS

Figure 1:
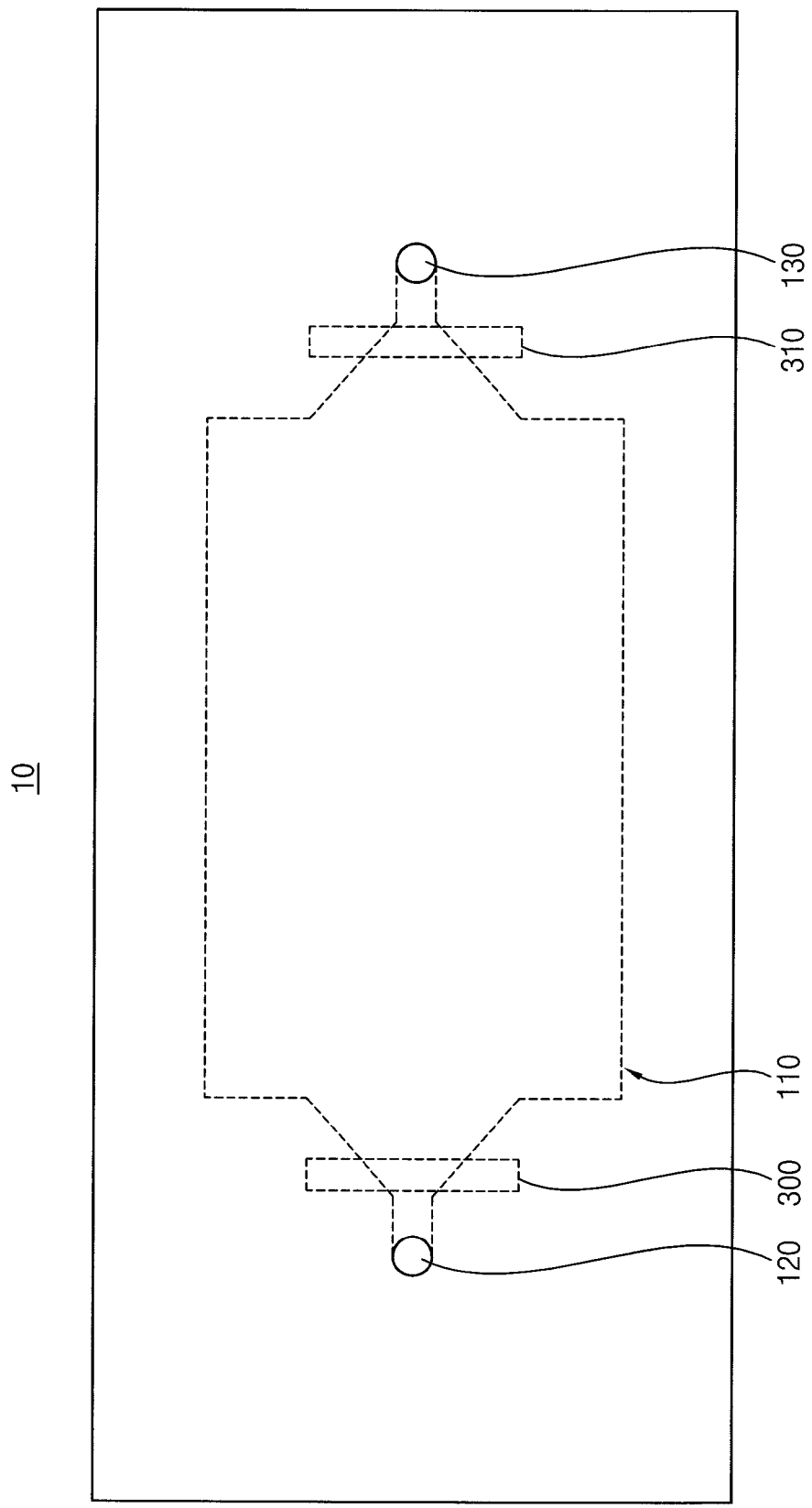

Various example embodiments will be described more fully hereinafter with reference to the accompanying drawings, in which some example embodiments are shown.

The present inventive concept may, however, be embodied in many different forms and should not be construed as limited to the example embodiments set forth herein. Rather, these example embodiments are provided so that this description will be thorough and complete, and will fully convey the scope of the present inventive concept to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third, fourth etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present inventive concept.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
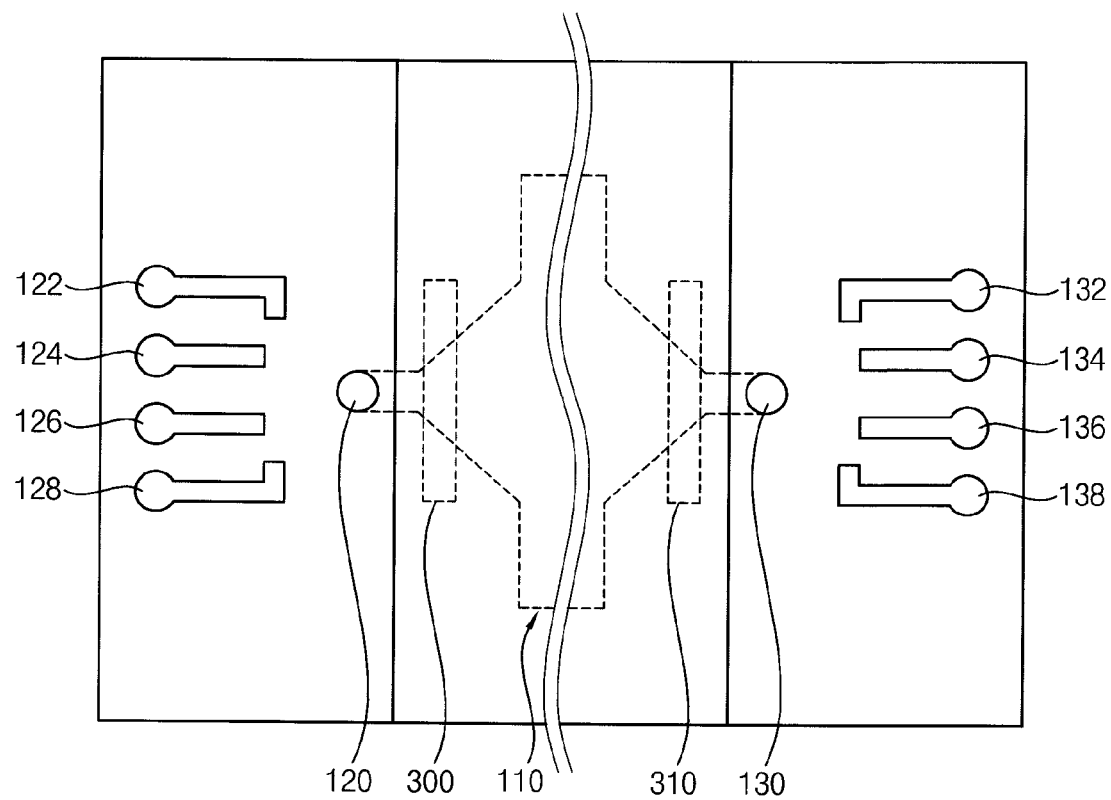

FIG. 1 is a plan view illustrating a particle processing device in accordance with an example embodiment. FIG. 2 is a plan view illustrating first and second input/output portions of the particle processing device in FIG. 1.

Referring to FIGS. 1 and 2, a particle processing device 10 may include a first input/output portion, a second input/output portion and a fluidic chamber 110 connected to the first and second input/output portions. The chamber 110 may provide a space for fluid flow. The chamber 110 may include at least one unit structure for selectively capturing and collecting particles in a fluid flowing through the chamber 110.

The first input/output portion may include a first port 120 through which a fluid having particles flows into or out of the chamber 110. The second input/output portion may include a second port 130 through which a fluid flows into or out of the chamber 110. The chamber 110 may be connected to the first port 120 and the second port 130 to provide a space for fluid flow.

In an example embodiment, the first input/output portion may include a first fluid supply element 122 for supplying a fluid into the chamber 110. The first fluid supply element 122 may be connected to the first port 120 to supply a fluid having particles. For example, the fluid may be a bodily fluid such as blood including cells of different types and biological particles. The fluid may include a target particle having information about the health of an organism. The target particle may be a biological micro-particle such as cell, bacteria, virus, etc.

The first input/output portion may further include a fluid transfer element for performing at least one function of pressure-supplying, releasing and draining. In particular, the first input/output portion may include a first pressure transfer element 124, a first release element 126 and a first drainage element 128.

For example, the first pressure transfer element 124 may provide a pressure for fluid flow from the first port 120 to the second port 130 in the chamber 110. In addition, the first pressure transfer element 124 may supply a predetermined pressure into a pneumatic membrane path formed in sidewalls of the chamber 110 or into a pneumatic membrane path formed in patterns of the unit structure. The first release element 126 may collect the particle that is selectively captured by the unit structure in the chamber 110. The first drainage element 128 may drain the fluid except the particle or a fluid for cleaning the chamber 110.

In an example embodiment, the second input/output portion may include a second fluid supply element 132 for supplying a fluid into the chamber 110. The second fluid supply element 132 may be connected to the second port 130 to supply a fluid for collecting particles.

The second input/output portion may further include a fluid transfer element for performing at least one function of pressure-supplying, releasing and draining. In particular, the second input/output portion may include a second pressure transfer element 134, a second release element 136 and a second drainage element 138.

For example, the second pressure transfer element 134 may provide a pressure for fluid flow from the second port 130 to the first port 120 in the chamber 110. In addition, the second pressure transfer element 134 may supply a predetermined pressure into a pneumatic membrane path formed in sidewalls of the chamber 110 or into a pneumatic membrane path formed in patterns of the unit structure. The second release element 136 may collect the fluid except the particle that is selectively captured by the unit structure in the chamber 110. The first drainage element 138 may drain a fluid for cleaning the chamber 110.

In an example embodiment, the first port 120 may be provided in a first side portion of the chamber 110 and the second port 130 may be provided in a second side portion of the chamber 100 opposite to the first side portion. Accordingly, the fluid may flow bidirectionally between the first and second side portions in the chamber 110.

For example, the fluid may flow from the first port 120 to the second port 130 in order to selectively capture particles in the fluid. The fluid may flow from the second port 130 to the first port 120 in order to collect the selectively captured particles.

As mentioned above, the first and second input/output portions may include hydrodynamic fluidic pressure for fluid flow in the chamber 110. For example, the first and second input/output portions may operate on the basis of mechanical principles (e.g. external syringe pumps, pneumatic membrane pumps, vibrating membrane pumps, vacuum devices, centrifugal forces, and capillary action), electrical or magnetic principles (e.g. electrohydrodynamic pumps and magenetohydrodynamic pumps), thermodynamic principles, etc.

In an example embodiment, the particle processing device 10 may further include at least one counter 300, 310 for detecting the number of the particles that are selectively captured. For example, a first counter 300 may be provided adjacent to the first port 120 and a second counter 310 may be provided adjacent to the second port 130. Alternatively, one counter may be arranged adjacent to any one of the first port 120 and the second port 130.

Figure 3A:
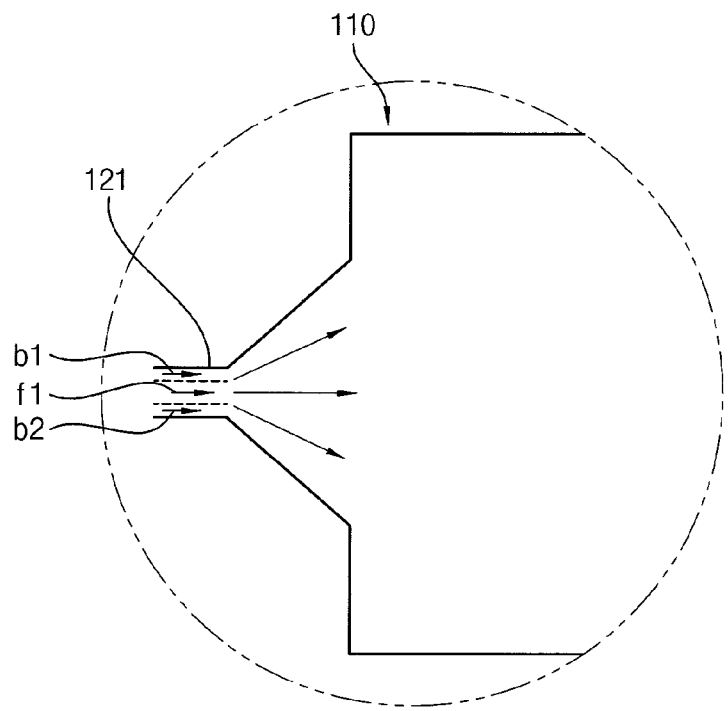
FIGS. 3A and 3B are plan views illustrating the first input/output portion in FIG. 1.
Figure 3B:
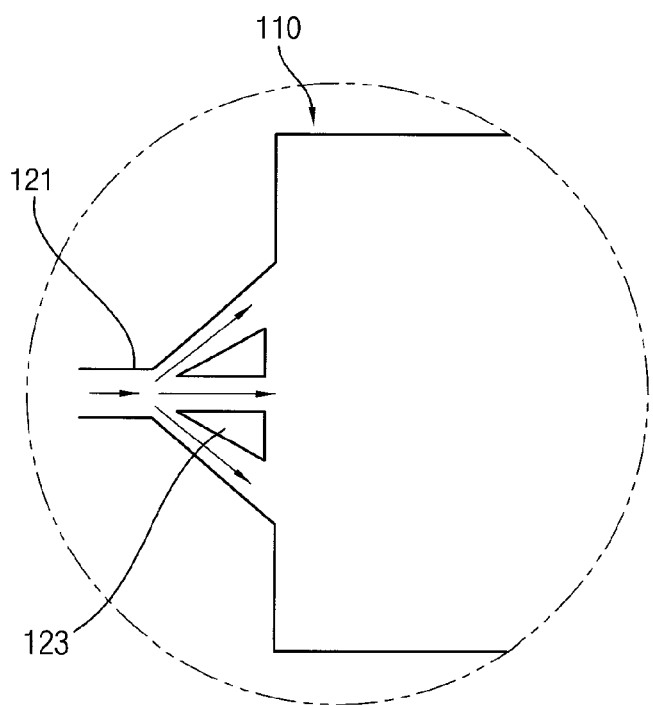

FIGS. 3A and 3B are plan views illustrating the first input/output portion in FIG. 1.

Referring to FIG. 3A, a fluid having particles may flow into the chamber 110 through a first path 121 of the first input/output portion. The fluid may be supplied into the chamber 110 by the first fluid supply element 122 and the fluid transfer element of the first input/output portion.

In an example embodiment, as illustrated in FIG. 3A, a fluid (f1) with buffer fluids (b1, b2) may flow in layers within the first path 121. Accordingly, the flow direction of the fluid may be controlled by the buffer fluids (b1, b2).

For example, the flow rate of the first buffer fluid (b1) may be greater than that of the second buffer fluid (b2). Accordingly, the flow direction of the fluid may be deflected toward the second buffer fluid (b2). Alternatively, the flow rate of the first buffer fluid (b1) may be less than that of the second buffer fluid (b2). Accordingly, the flow direction of the fluid may be deflected toward the first buffer fluid (b1).

Referring to FIG. 3B, in an example embodiment, the first input/output portion may further include a guide structure 123 for controlling the flow direction of the fluid. For example, a pair of guide structures 123 may be provided adjacent to the first path 121 in a diffusion region of the chamber 110.

The fluid having particles may flow the first path 121 and enter the diffusion region of the chamber 110. The fluid may enter the chamber 110 along the boundaries of the guide structures 123. Accordingly, the flow direction of the fluid may be controlled by a pair of the guide structures 123 in the diffusion region.

Figure 4:
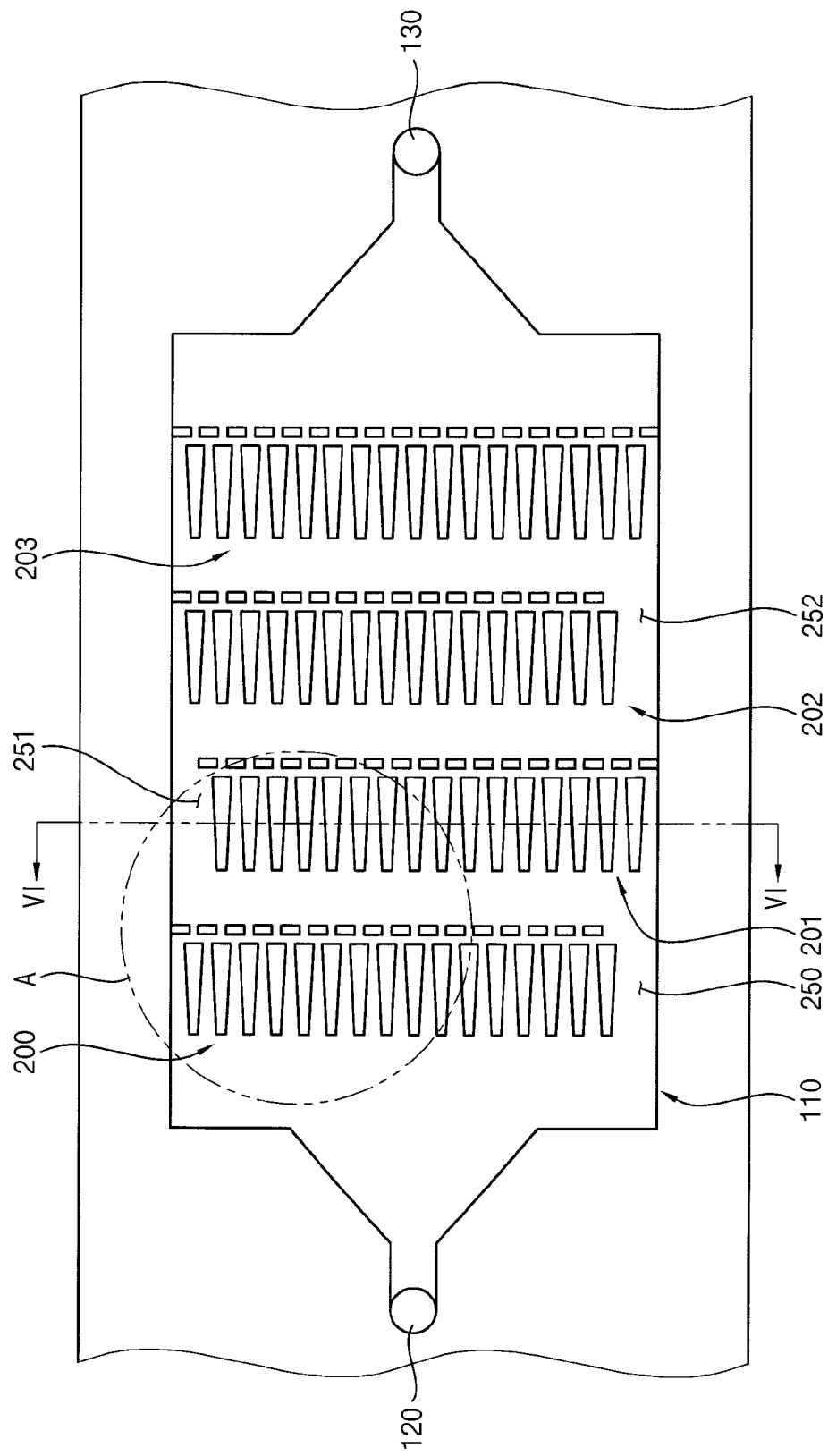
Figure 5:
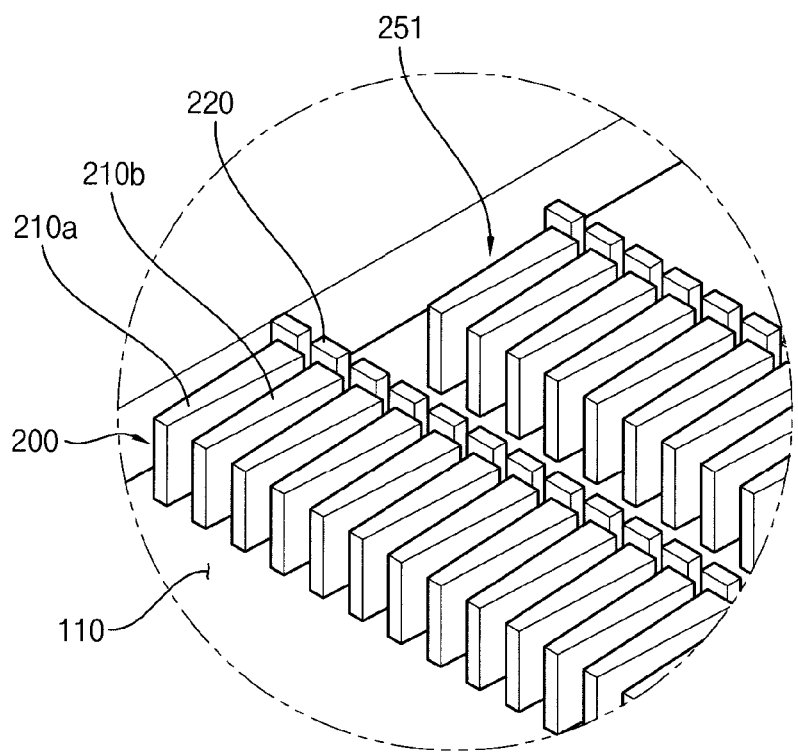
Figure 6:
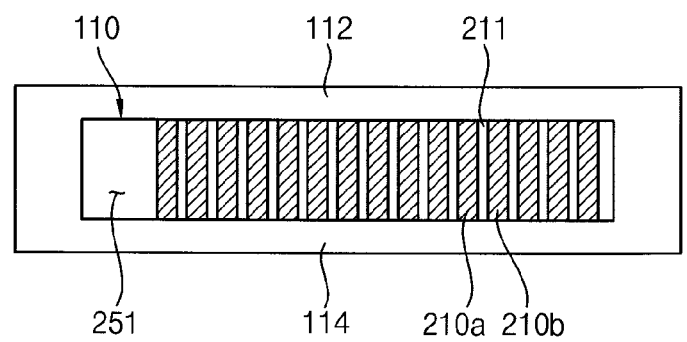

FIG. 4 is a plan view illustrating the chamber of the particle processing device in FIG. 1. FIG. 5 is an enlarged perspective view illustrating the "A" portion in FIG. 4. FIG. 6 is a cross-sectional view taken along the VI-VI' line in FIG. 4.

Referring to FIGS. 4 to 6, the particle processing device 10 may include at least one channel array capable of selectively capturing and collecting particles in a fluid. The channel array may be provided in the chamber 110. The channel array may include a plurality of unit structures. The unit structure may selectively capture and collect particles in a fluid flowing in the chamber 110.

In an example embodiment, first, second, third and fourth channel arrays 200, 201, 202, 203 may be sequentially arranged in a direction from the first port 120 to the second port 130 in the chamber 110.

The fluid flows in a first flow direction from the first port 120 to the second port 130 within the chamber 110 such that the fluid sequentially passes the first, second, third and fourth channel arrays 200, 201, 202, 203. In here, the first flow direction may be the flow direction for capturing particles in the fluid.

The fluid flows in a second flow direction from the second port 130 to the first port 120 such that the fluid sequentially passes the fourth, third, second and first channel arrays 203, 202, 201, 200. In here, the second flow direction may be the flow direction for collecting the captured particles.

In this case, the unit structures of the channel array may be arranged such that fluidic channels of the unit structures may be substantially parallel with the flow direction of the fluid.

The first channel array 200 may include a plurality of first unit structures. The second channel array 201 may include a plurality of second unit structures. The third and fourth channel arrays 202, 203 may include a plurality of unit structures the same as or similar to the first and second unit structures.

In an example embodiment, the first unit structure may include a first capturing structure and a first auxiliary structure. The second unit structure may include a second capturing structure and a second auxiliary structure. The second capturing structure may be substantially the same as or similar to the first capturing structure. The second auxiliary structure may be substantially the same as or similar to the first auxiliary structure.

The first capturing structure may have a fluidic channel defining a capturing region in which particles are captured from a fluid flowing from the first port 120 to the second port 130. The first auxiliary structure may be arranged adjacent to the first capturing structure. The first auxiliary structure may prevent undesired particles from flowing into the fluidic channel of the capturing structure when a collection fluid flows from the second port 130 to the first port 120. The unit structure will be explained later in detail with reference to FIG. 7.

In an example embodiment, the particle processing device 10 may further include at least one auxiliary path 250, 251, 252 for controlling the fluid flow in the chamber 110. The auxiliary pathes 250, 251, 252 may control the flow rate of the fluid passing through the channel arrays and the flow direction of the fluid in the chamber 110.

As illustrated in FIG. 4, a first auxiliary path 250 may be arranged adjacent to the first channel array 200. The first auxiliary path 250 and the first channel array 200 may be arranged in the same row. The first auxiliary path 250 may be provided in a peripheral region of the first channel array 200. Alternatively, the first auxiliary path 250 may be provided in the middle region of the first channel array 200. The first auxiliary path 250 may provide a space for an additional fluid flow to control the flow rate or flow direction of the fluid flowing through the first channel array 200.

A second auxiliary path 251 may be arranged adjacent to the second channel array 201. The second auxiliary path 251 and the second channel array 201 may be arranged in the same row. The second auxiliary path 251 may provide a space for an additional fluid flow to control the flow rate or flow direction of the fluid flowing through the second channel array 201.

A third auxiliary path 252 may be arranged adjacent to the third channel array 202. The third auxiliary path 252 and the third channel array 202 may be arranged in the same row. The third auxiliary path 252 may provide a space for an additional fluid flow to control the flow rate or flow direction of the fluid flowing through the third channel array 202.

In an example embodiment, the unit structure of the channel array may be formed between opposing sidewalls (upper and lower sidewalls 112, 114) of the chamber 110. As illustrated in FIG. 6, the unit structure may include a pair of channel patterns 210a, 210b to define a fluidic channel 211 between the upper and lower sidewalls 112, 114 of the chamber 110. A pair of the channel patterns 210a, 210b may be patterns between the sidewalls of the chamber 110 to extend along the flow direction of a fluid.

The patterns may be formed by semiconductor manufacture processes including photolithography, growth and etching of crystal structure. For example, the chamber 110 and the channel array may be formed using polymer material, inorganic material, etc. Examples of the polymer material may be PDMS (polydimethylsiloxane), PMMA (polymethylmethacrlyate), etc. The examples of the inorganic material may be glass, quartz, silicon, etc.

Figure 7:
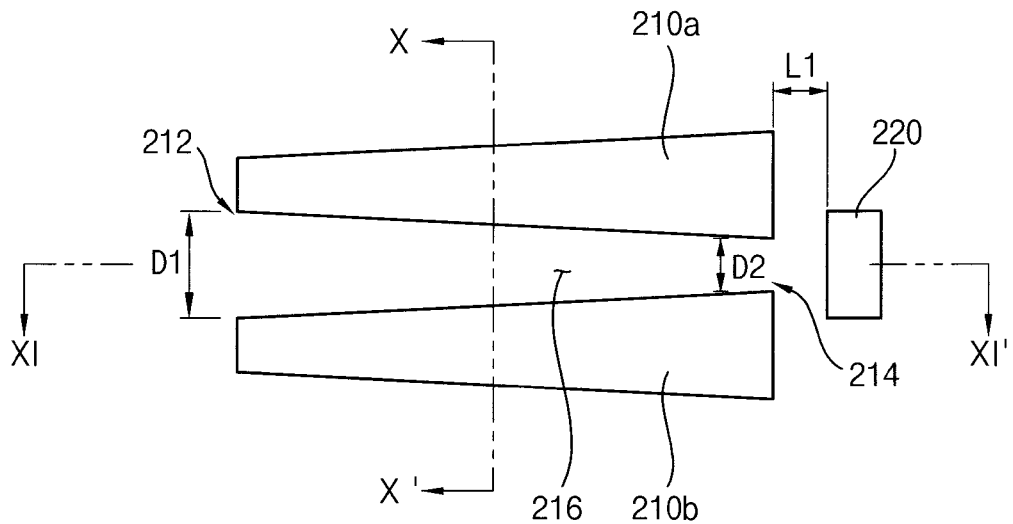

FIG. 7 is a plan view illustrating the unit structure of the particle processing device in accordance with an example embodiment.

Referring to FIGS. 5 and 7, the unit structure of the particle processing device 10 may include at least one capturing structure provided in the chamber 110.

In an example embodiment, the capturing structure may include a pair of the channel patterns formed between the upper and lower sidewalls of the chamber 110. A pair of the channel patterns may include a first channel pattern 210a and a second channel pattern 210b. The opposing first and second channel patterns 210a, 210b may extend between the sidewalls of the chamber 110 to form the fluidic channel.

The fluidic channel may have a first opening 212 and a second opening 214 through which a fluid flow into or out of the fluidic channel. The distance between the first and second channel patterns 210a, 210b may be changed along the extending directions thereof. Accordingly, the fluidic channel may include a capturing region 216 having a changeable sectional shape between the first opening 212 and the second opening 214.

In an example embodiment, the first opening 212 may have a first size and the second opening 214 may have a second size smaller than the first size. The second size of the second opening 214 may be smaller than the minimum size of the particle that is deformed under a local pressure due to the physical characteristics of the particle such as deformability or stiffness.

For example, the first opening 212 may have a first diameter (D1) or a first width. The second opening 214 may have a second diameter (D2) smaller than the first diameter (D1) or a second width smaller than the first width. In this case, the sectional profile of the capturing region 216 may be decreased gradually from the first opening 212 to the second opening 214. That is, the capturing region 216 may have a changeable sectional shape, the sectional area of which is decreased gradually in the first flow direction.

When a fluid moves from the first port 120 to the second port 130, the fluid may pass through the fluidic channel of the capturing structure. In this case, the fluid may flow into the first opening 212, move through the capturing region 216, and then flow out of the second opening 214.

In an example embodiment, the second diameter (D2) of the second opening 214 may be smaller than the minimum diameter of the particle that is deformed by a local pressure. The first diameter (D1) of the first opening 212 may be greater than the minimum diameter of the particle that is deformed.

Accordingly, when the fluid flows through the fluidic channel of the capturing structure from the first port 120 to the second port 130, the particle may not pass the fluidic channel but remain to be captured in the capturing region 216. The particle that is captured in the capturing region 216 may be collected by a collection fluid that flows from the second port 130 to the first port 120.

In an example embodiment, the unit structure of the particle processing device 10 may further include at least one auxiliary structure adjacent to the capturing structure in the chamber 110. The auxiliary structure may be at least one auxiliary structure pattern 220 between the upper and lower sidewalls of the chamber 110.

The auxiliary structure may be arranged adjacent to the second opening 214 of the fluidic channel of the capturing structure. The auxiliary structure may be spaced apart from the second opening 214 by a first distance (L1). For example, the first distance (L1) may be smaller than the minimum diameter of the particle that is deformed. Accordingly, the auxiliary structure may be used to efficiently collect the particle that is captured in the capturing region 216 of the capturing structure.

In particular, when a collection fluid flows from the second port 130 to the first port 120 in order to collect the captured particle, the auxiliary structure may prevent undesired particles from flowing into the fluidic channel of the capturing structure.

Accordingly, the auxiliary structure may selectively allow or prevent entering of specific particles into the fluidic channel according to the moving direction of the particles between the first port 120 and the second port 130.

Figure 8A:
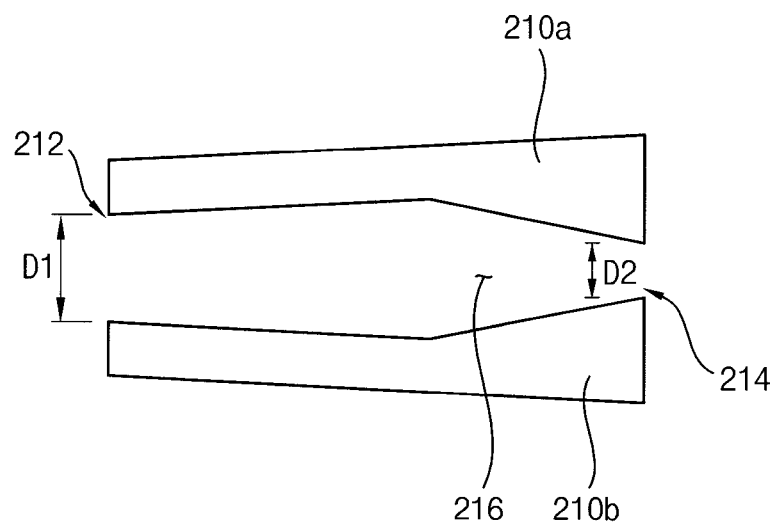
FIGS. 8A to 8C are plan views illustrating various shapes of a capturing structure.
Figure 8B:
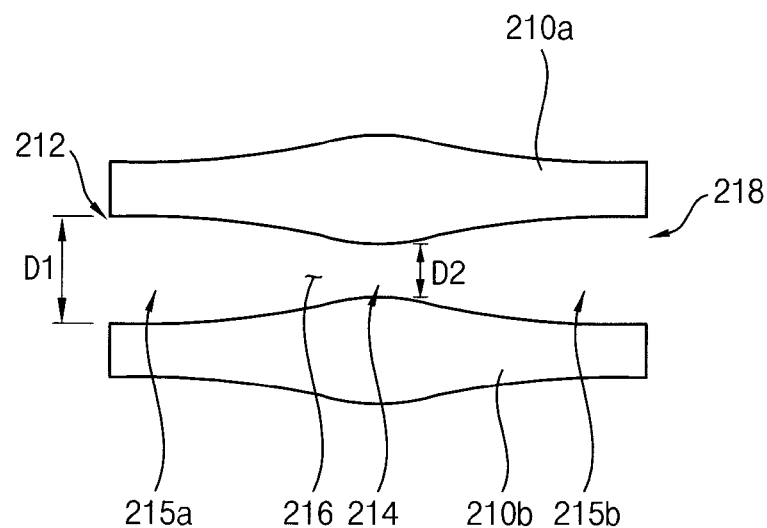
Figure 8C:
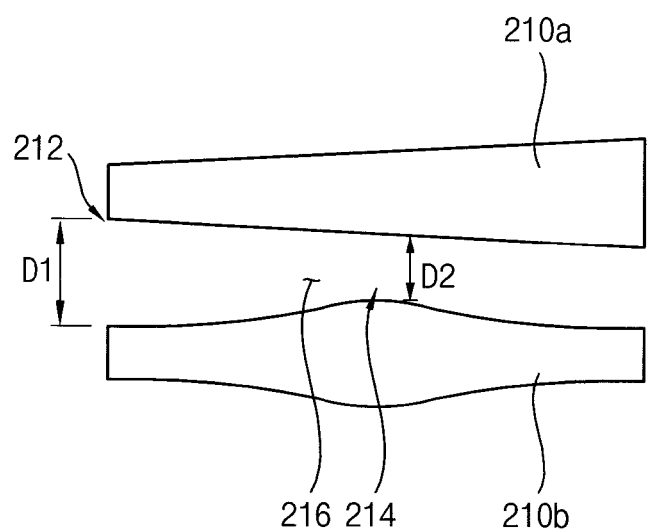

FIGS. 8A to 8C are plan views illustrating various shapes of a capturing structure.

Referring to FIG. 8A, first and second channel patterns 210a, 210b of a capturing structure may be formed such that a sectional shape between the first and second channel patterns 210a, 210b may be increased and then decreased from a first opening 212 to a second opening 214. In this case, a capturing region 216 of the capturing structure may have a gradually decreasing sectional shape.

Referring to FIG. 8B, first and second channel patterns 210a, 210b of a capturing structure may be formed to have a first channel region 215a and a second channel region 215b. The first channel region 215a may have a gradually decreasing sectional shape from a first opening 212 to a second opening 214. The second channel region 215b may have a gradually increasing sectional shape from the second opening 214 to a third opening 218. In this case, a capturing region 216 of the capturing structure may be defined in the first channel region 215a.

Referring to FIG. 8C, first and second channel patterns 210a, 210b of a capturing structure may be formed to be asymmetric. The width of the first channel pattern 210a may be gradually increased along the extending direction thereof. The width of the second channel pattern 210b may be gradually increased and then decreased along the extending direction thereof. In this case, a second diameter (D2) may be defined between the first and second channel patterns 210a, 210b in a region having a diameter smaller than the minimum diameter of the particle that is deformed.

Accordingly, the first and second channel patterns 210a, 210b having a changeable width along the extending direction thereof may define at least one of the first and second openings 212, 214.

Figure 9A:
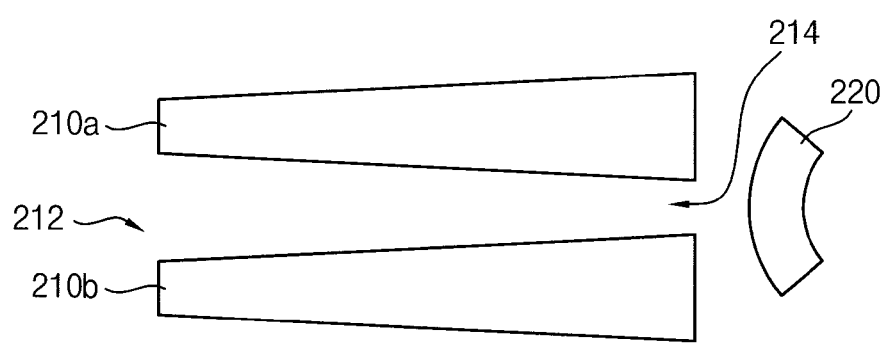
FIGS. 9A and 9B are plan views illustrating various shapes of an auxiliary structure.
Figure 9B:
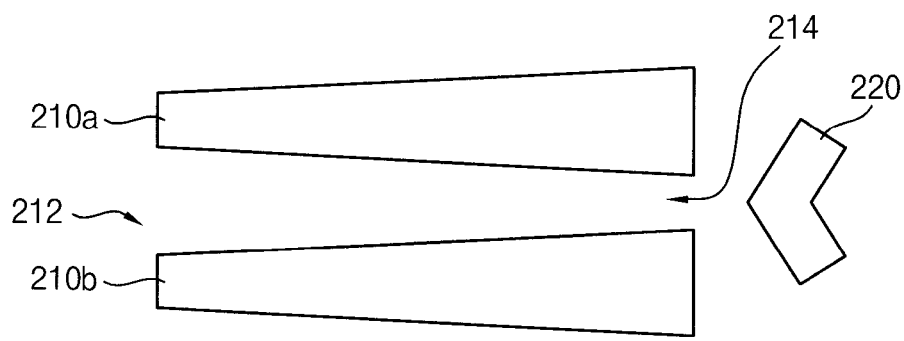

FIGS. 9A and 9B are plan views illustrating various shapes of an auxiliary structure.

Referring to FIGS. 9A and 9B, an auxiliary structure pattern 220 may have an arc shape or a V shape. In this case, the minimum distance between the auxiliary structure pattern 220 and the capturing structure may be attained at the middle point of a second opening and the distance between the auxiliary structure pattern 220 and the capturing structure may be increased gradually from the middle point to a peripheral region of the second opening.

Accordingly, the auxiliary structure may make a collection fluid flow smoothly in the fluidic channel to thereby efficiently collect the captured particle.

FIGS. 10A to 10D are cross-sectional views illustrating modified capturing structures, viewed along the X-X' line in FIG. 7.

Figure 10A:
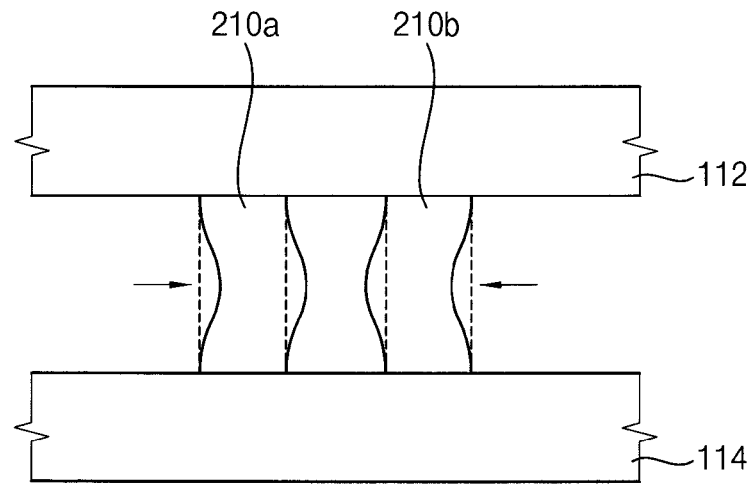
FIGS. 10A to 10D are cross-sectional views illustrating modified capturing structures, viewed along the X-X' line in FIG. 7.
Figure 10B:
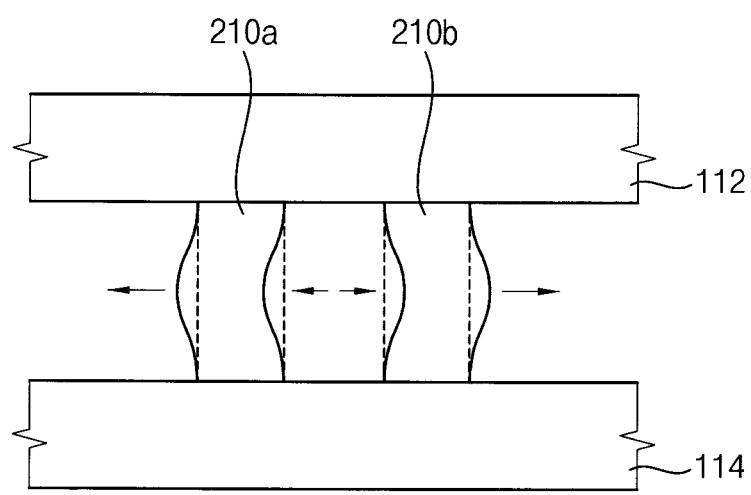

Referring to FIGS. 10A and 10B, at least one of first and second channel patterns 210a, 210b of a capturing structure may be deformed by an externally exerted force or pressure to change an opening size of the fluidic channel. For example, the first and second channel patterns 210a, 210b may include a deformable polymer material. As illustrated in FIGS. 10A and 10B, the first and second channel patterns 210a, 210b may be deformed by a hydraulic pressure to change the opening size of the fluidic channel.

Figure 10C:
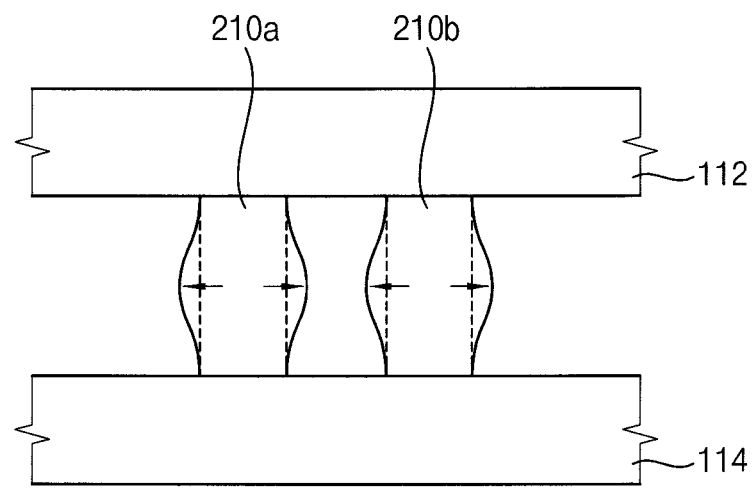

Referring to FIG. 10C, at least one of first and second channel patterns 210a, 210b of a capturing structure may be deformed by a pneumatic pressure. For example, the first and second channel patterns 201a, 210b including a deformable polymer material may include a pneumatic line formed therein.

When the pneumatic line formed in the opposing first and second channel patterns 210a, 210b is filled with a gas, the first and second channel patterns 210a, 210b may expand laterally such that the fluidic channel may have a changeable sectional shape. Accordingly, the first and second channel patterns 210a, 210b may be deformed by a pneumatic pressure to define a diameter (size) of any one of first and second openings of the fluidic channel.

Figure 10D:
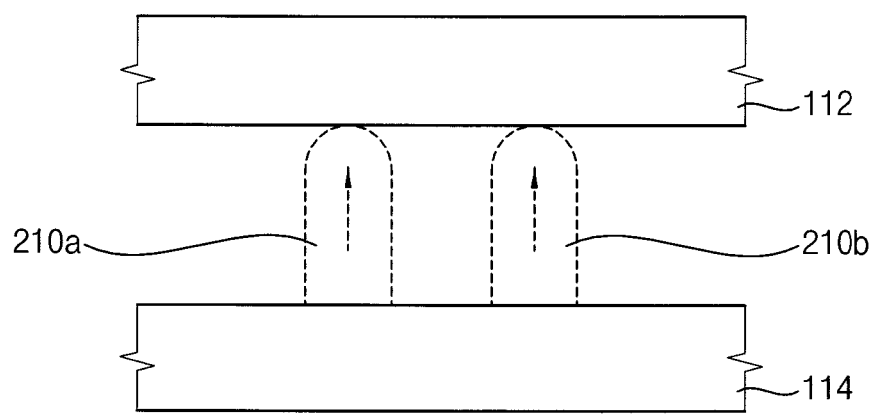

Referring to 10D, at least one of first and second channel patterns 210a, 210b of a capturing structure may be deformed by an externally exerted force or pressure to be generated or removed. As illustrated in FIG. 10D, when a pneumatic line formed in the first and second channel patterns 210a, 210b is filled with a gas, the first and second channel patterns 210a, 210b may expand vertically to be generated such that a fluidic channel may be formed between the opposing sidewalls 112, 114. On the other hand, when the gas is discharged from the pneumatic line formed in the first and second channel patterns 210a, 210b, the first and second channel patterns 210a, 210b may contract vertically to be removed.

Figure 11A:
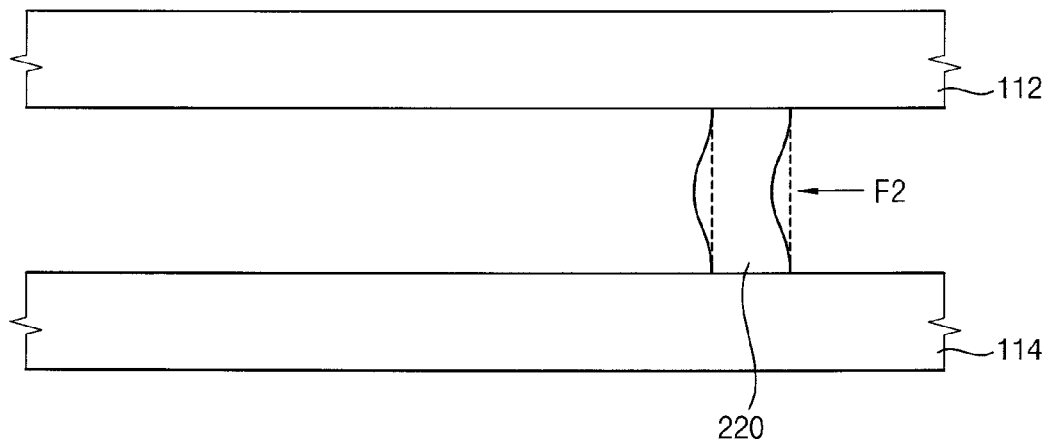
FIGS. 11A to 11C are cross-sectional views illustrating modified auxiliary structures, viewed along the XI-XI' line in FIG. 7.
Figure 11B:
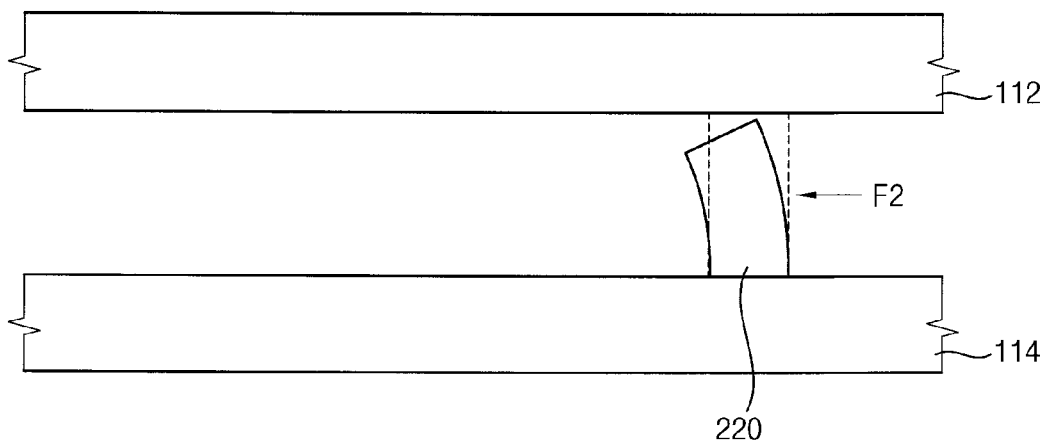
Figure 11C:
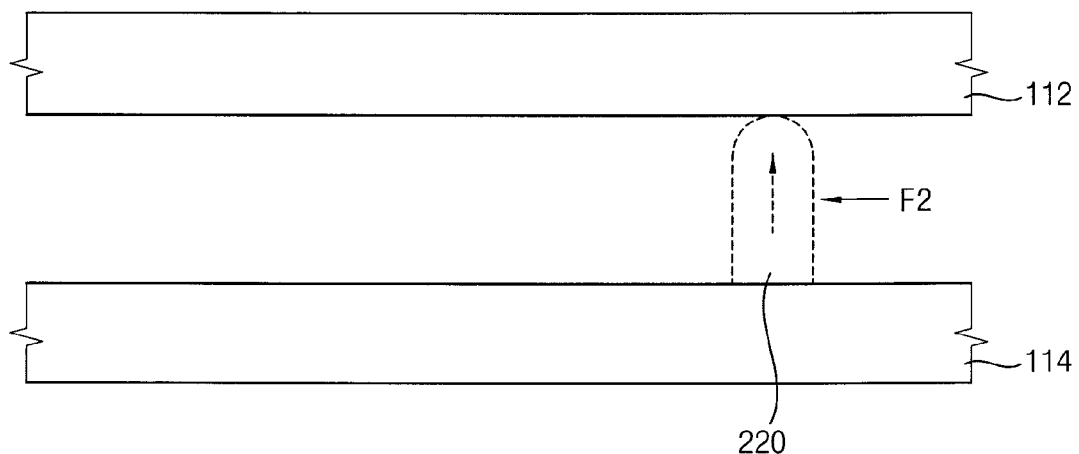

FIGS. 11A to 11C are cross-sectional views illustrating modified auxiliary structures, viewed along the XI-XI' line in FIG. 7.

Referring to FIGS. 11A and 11B, an auxiliary structure may be deformed by an externally exerted force or pressure. The auxiliary structure pattern 220 formed between upper and lower sidewalls 112, 114 of a chamber 110 may be deformed by a fluid flowing in the second flow direction (F2), that is, from the second port 130 to the first port 120. When the fluid flows from the second port 130 to the first port 120, the auxiliary structure pattern 220 may be deformed toward the second opening 214 of the capturing structure. Accordingly, the distance between the auxiliary structure pattern 220 and the capturing structure may be decreased by the fluid flowing form the second port 130 to the first port 120.

Although it is not illustrated in the figure, when the fluid flows in the first flow direction, that is, from the first port 120 to the second port 130, the auxiliary structure pattern 220 may be deformed to be far from the second opening 214 of the capturing structure. Accordingly, the distance between the auxiliary structure pattern 220 and the capturing structure may be increased by the fluid flowing form the first port 120 to the second port 130.

Referring to FIG. 11C, an auxiliary structure may be deformed by an externally exerted force or pressure to be generated or removed. The auxiliary structure may be deformed by a pneumatic pressure. For example, the auxiliary structure pattern 220 including a deformable polymer material may include a pneumatic line formed therein.

The auxiliary structure pattern 220 may be formed in a lower sidewall 114 of a chamber 110. The auxiliary structure pattern 220 may be spaced apart from an upper sidewall 112 of the chamber 110. When the pneumatic line formed in the auxiliary structure pattern is filled with a gas, the auxiliary structure pattern 220 may expand vertically to be generated such that the auxiliary structure pattern 220 may make contact with the upper sidewall 112 of the chamber 110. Accordingly, the auxiliary structure may prevent undesired particles from flowing into the fluidic channel of the capturing structure, when a fluid flows from the second port 130 to the first port 120.

Alternatively, although it is not illustrated in the figure, when a pneumatic line formed in the auxiliary structure pattern 220 is filled with a gas, the auxiliary structure pattern 220 may expand laterally toward the second opening 214 of the capturing structure. Accordingly, the distance between the auxiliary structure pattern 220 and the capturing structure may be decreased by the pneumaticle pressure.

Figure 12:
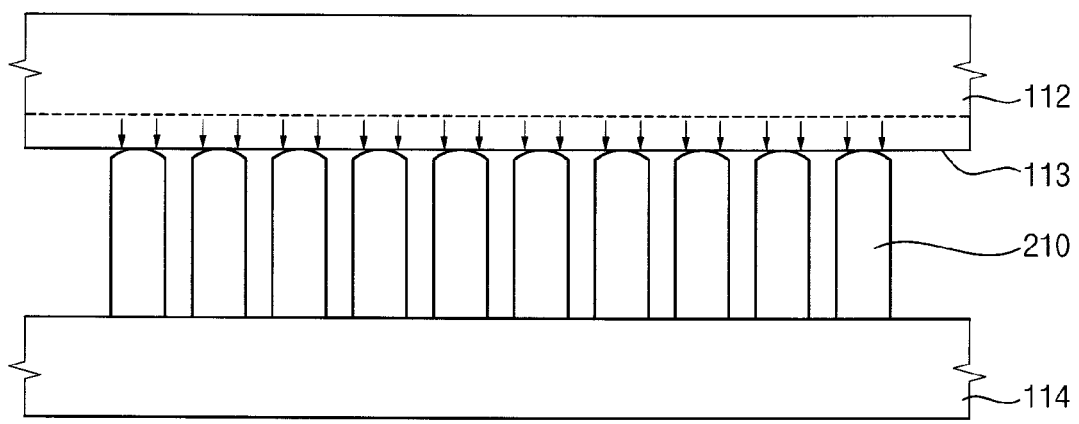

FIG. 12 is a cross-sectional view illustrating a modified chamber.

Referring to FIG. 12, unit structures may be formed on a lower sidewall 114 of a chamber 110. The unit structures may be spaced apart from an upper sidewall 112 of the chamber 110. As illustrated in FIG. 12, capturing structures may be formed on the lower sidewall 114 of the chamber 110 and the capturing structures may be spaced apart from the upper sidewall 112.

In this case, any one of the sidewalls of the chamber 110 may be deformed by an external force such that the deformed sidewall and the channel patterns 210a, 210b of the capturing structure form a fluidic channel.

In particular, the upper sidewall 112 of the chamber 110 may be deformed by a pneumatic pressure. For example, the upper sidewall 112 of the chamber 110 including a deformable polymer material may include a pneumatic line formed therein. When the pneumatic line formed in the upper sidewall 112 of the chamber 110 is filled with a gas, the upper sidewall 112 may expand down such that the upper sidewall 112 may make contact with the capturing structure. The upper sidewall 112 of the chamber 110 may expand by a pneumatic pressure to contact the capturing structure, to thereby provide fluidic channels between the upper and lower sidewalls 112, 114 of the chamber 110.

Figure 13A:
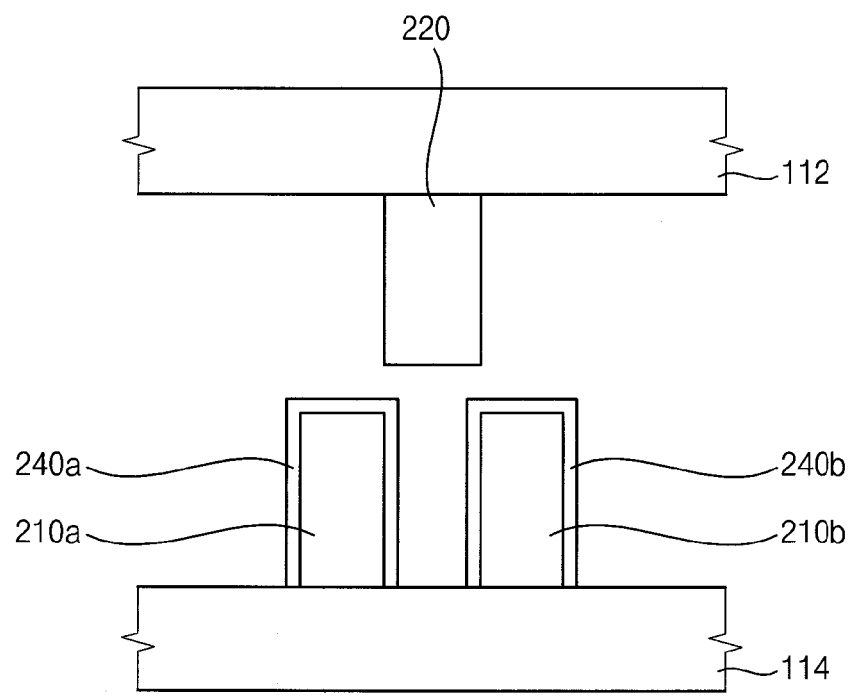
FIGS. 13A and 13B are cross-sectional views illustrating modified unit structures.
Figure 13B:
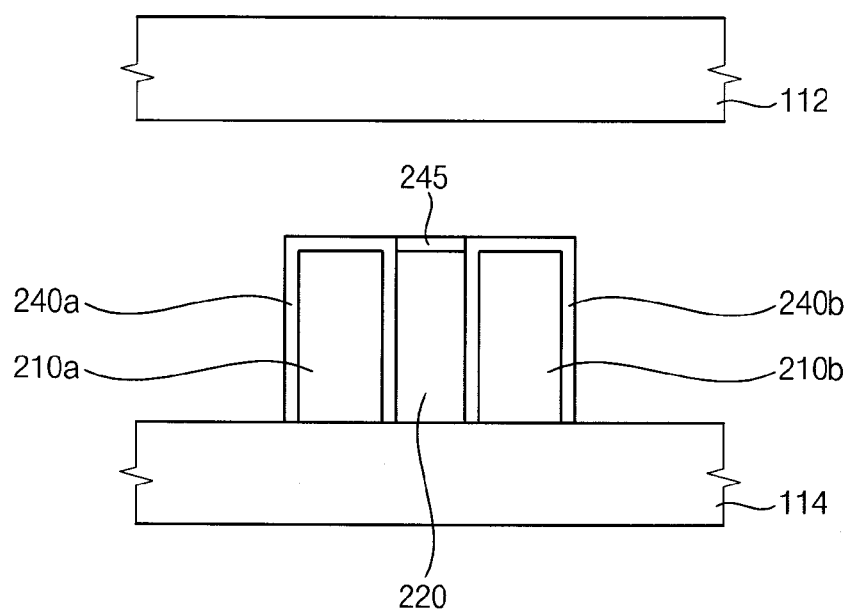

FIGS. 13A and 13B are cross-sectional views illustrating modified unit structures.

Referring to FIGS. 13A, 13B, a unit structure may further include a biochemical material layer that is formed on at least one of the capturing structure and the auxiliary structure. Alternatively, surface treatment may be performed on the at least one of the capturing structure and the auxiliary structure to change biochemical surface characteristics or physical surface characteristics such as surface roughness.

As illustrated in FIG. 13A, material layers 240a, 240b may be formed on the channel patterns 210a, 210b that are formed on the lower sidewall 114 of the chamber. In this case, the auxiliary structure pattern 220 may be formed on the upper sidewall 112. After the material layers 240a, 240b are formed on the channel patterns 210a, 210b, the upper sidewall 112 and the lower sidewall 114 may be combined with each other to form a fluidic channel. Accordingly, the biochemical material layers 240a, 240b may be formed on a surface of the fluidic channel defined by the channel patterns 210a, 210b to increase the adhesive strength with the target particle.

Although it is not illustrated in the figures, different biochemical material layer may be formed on the auxiliary structure pattern 220. In here, the biochemical material layer on the auxiliary structure pattern 220 may decrease the adhesive strench with the target particle.

As illustrated in FIG. 13B, material layers 240a, 240b, 245 may be formed respectively on the channel patterns 210a, 210b and the auxiliary structure pattern 220 that are on the lower sidewall of the chamber. After the material layers 240a, 240b, 245 are formed on the channel patterns 210a, 210b and the auxiliary structure pattern 220 respectively, the upper sidewall 112 and the lower sidewall 114 may be combined with each other to form a fluidic channel. Accordingly, the biochemical material layers 240a, 240b, 245 may increase or decrease the adhesive strength with the target particle to efficiently capture and collect the target particle in a fluid.

FIG. 14 is a plan view illustrating a modified particle processing device.

Referring to FIG. 14, the first input/output portion may further include a first filter 400 and the second input/output portion may further include a second filter 410. The first filter 400 may be arranged adjacent to the first port 120 and the second filter 410 may be arranged adjacent to the second port 130.

The first filter 400 may filter a fluid flowing between the first port 120 and the chamber 110. The second filter 410 may filter a fluid flowing between the second port 130 and the chamber 110.

The first filter may have an opening having a size greater than the first opening of the fluidic channel of the capturing structure. For example, the opening of the first filter may have a diameter greater than the first diameter of the first opening of the fluidic channel. The second filter may have an opening having a size smaller than the second opening of the fluidic channel of the capturing structure. For example, the opening of the second filter may have a diameter smaller than the second diameter of the second opening of the fluidic channel.

Accordingly, the first and second filters may prevent undesired particles from flowing into the chamber 110.

Figure 15A:
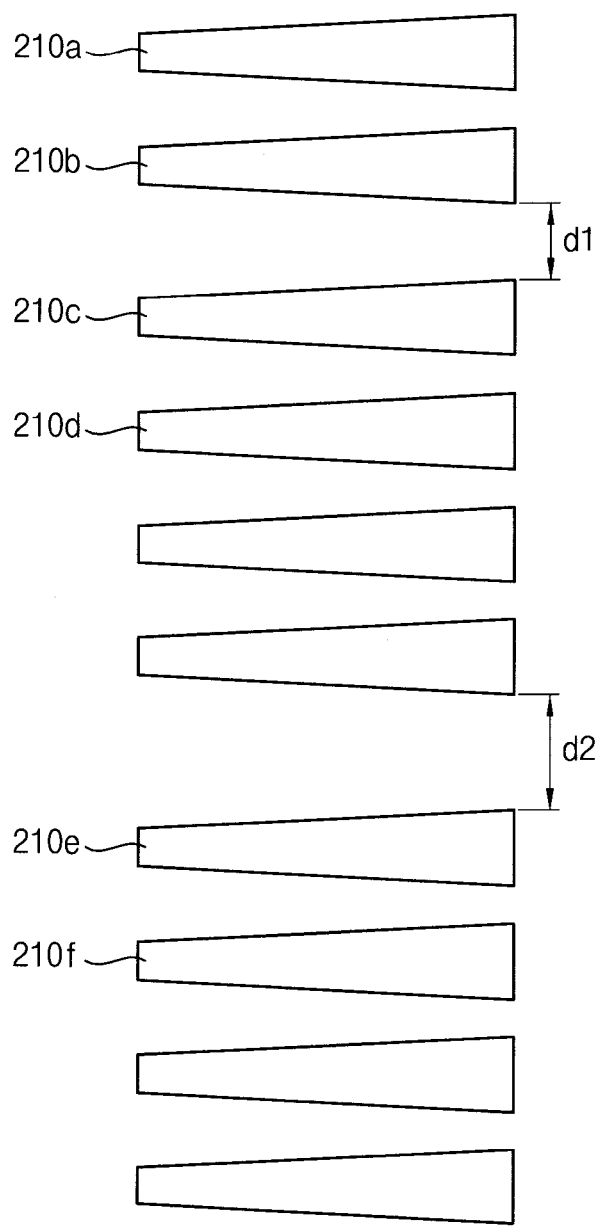
FIGS. 15A and 15B are plan views illustrating various arrangements of capturing structures of a channel array.
Figure 15B:
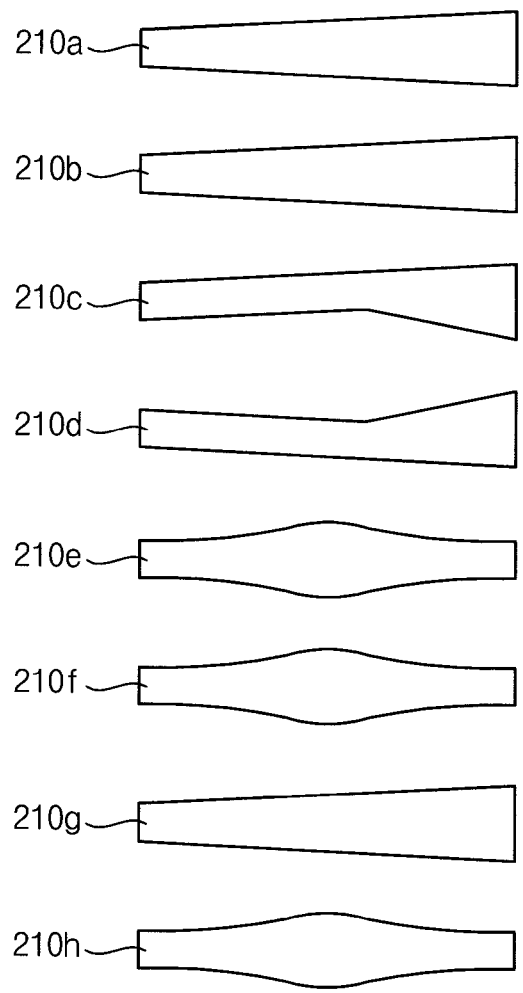

FIGS. 15A and 15B are plan views illustrating various arrangements of capturing structures of a channel array.

Referring to FIG. 15A, capturing structures of a channel array may include channel patterns that are spaced apart from one another by different distances. For example, a pair of the first and second channel patterns 210a, 210b may be spaced apart from a pair of the first and second channel patterns 210c, 210d by a first distance (d1). A pair of the first and second channel patterns 210e, 210f may be spaced apart from an adjacent pair of channel patterns by a second distance (d2).

Referring to FIG. 15B, capturing structures of a channel array may include channel patterns having different shapes.

For example, the opposing first and second channel patterns 210a, 210b may be symmetric and the widths of the first and second channel patterns 210a, 210b may be gradually increased along the extending directions thereof. A channel region formed by first and second channel patterns 210c, 210d may have a sectional shape that is gradually increased and then decreased. Widths of first and second channel patterns 210e, 210f may be gradually increased and then decreased along the extending directions thereof. First and second channel patterns 210g, 210h may be asymmetric, the width of the first channel pattern 210g may be gradually increased along the extending direction thereof and the width of the second channel pattern 210h may be gradually increased and then decreased along the extending direction thereof.

Figure 16A:
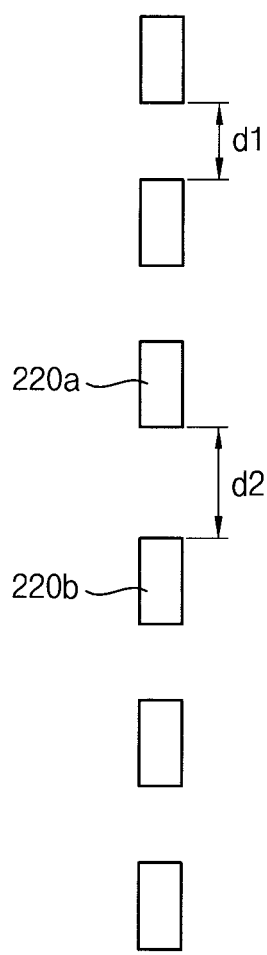

FIGS. 16A and 16B are plan views illustrating various arrangements of auxiliary structures of channel array.

Referring to FIG. 16A, auxiliary structures of a channel array may include auxiliary structure patterns that are spaced apart from one another by different distances. For example, an auxiliary structure pattern 220a may be spaced apart from an adjacent auxiliary structure pattern by a first distance (d1). Another auxiliary structure pattern 220b may be spaced apart from the adjacent auxiliary structure pattern 220a by a second distance (d2).

Referring to FIG. 16B, auxiliary structures of a channel array may include auxiliary structure patterns having different shapes.

For example, an auxiliary structure pattern 220a may have a rectangular plate shape. An auxiliary structure pattern 220b may have an arc shape. An auxiliary structure pattern 220c may have a V shape.

Figure 17:
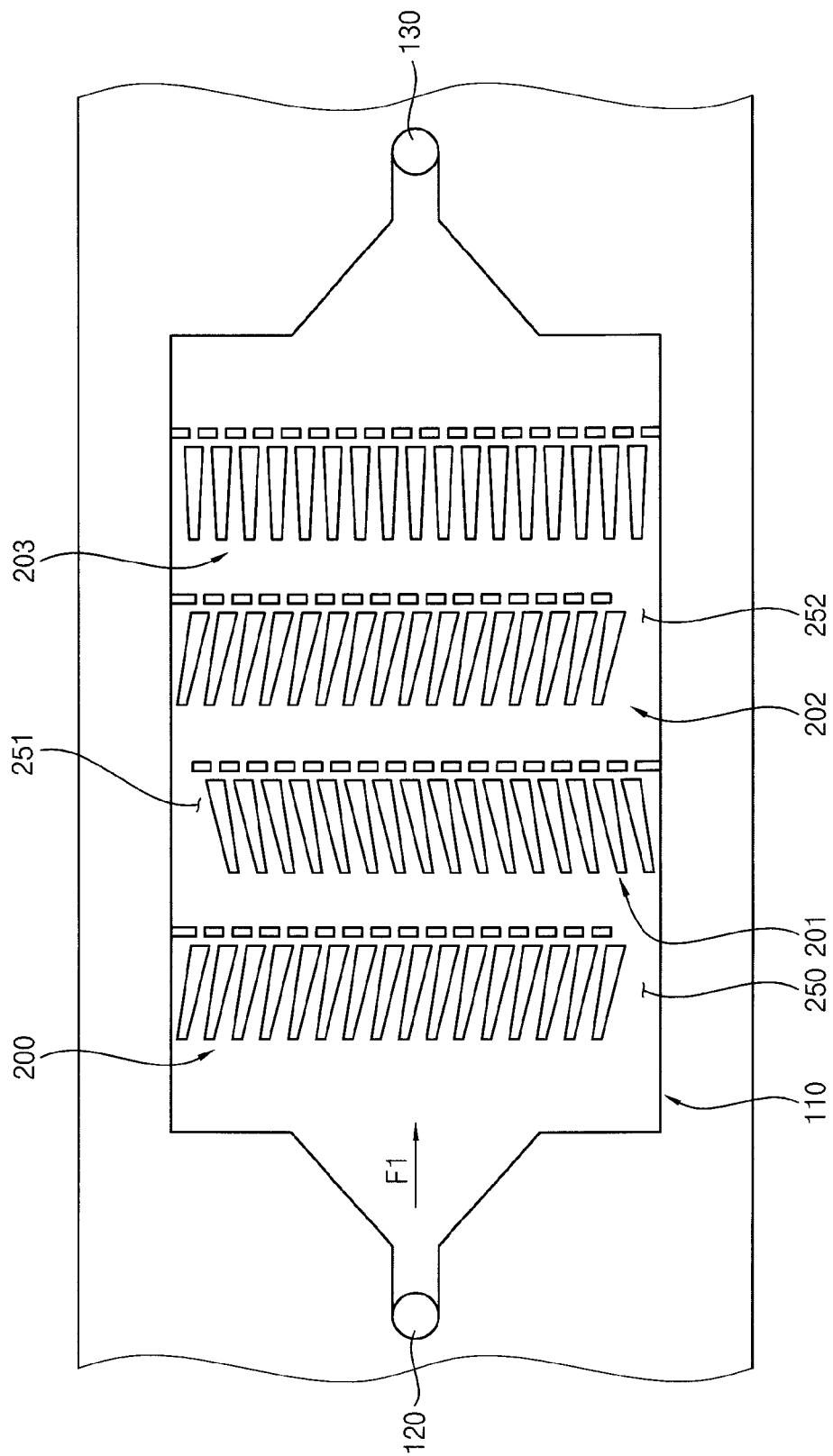

FIG. 17 is a plan view illustrating modified channel arrays in a chamber.

Referring to FIG. 17, channel arrays may include a plurality of unit structures that are arranged inclined at different angles with respect to a flow direction. The unit structure may be arranged inclined at a predetermined angle with respect to a first flow direction (F1).

For example, first and third channel arrays 200, 202 may include a plurality of unit structures that are arranged inclined at a negative angle with respect to the first flow direction (F1). The second channel array 201 may include a plurality of unit structures that are arranged inclined at a positive angle with respect to the first flow direction (F1). It can be understood that the inclination angle may not be limited thereto, but may be determined based on the flow direction and a flow rate of a fluid, etc.

Figure 18A:
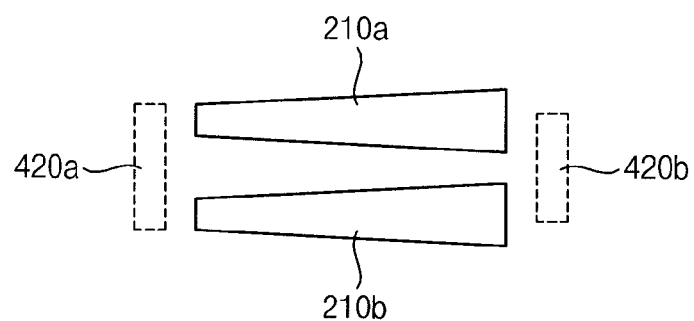
FIGS. 18A and 18B are plan views illustrating a counter provided in the particle processing device in FIG. 1.
Figure 18B:
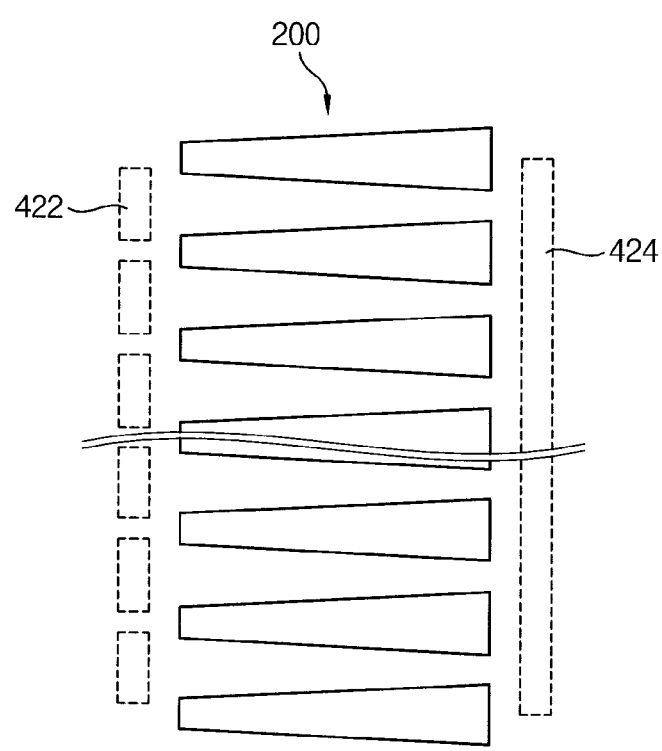

FIGS. 18A and 18B are plan views illustrating a counter provided in the particle processing device in FIG. 1.

Referring FIG. 18A, a particle processing device may further include a counter that is provided in a unit structure to detect the number of the particles that are selectively captured in the unit structure.

For example, third counters 420a, 420b may be provided in an inlet and an outlet (first and second openings) of a fluidic channel defined by channel patterns 210a, 210b to detect the number of the particles that are captured in the fluidic channel.

Referring to FIG. 18B, a particle processing device may further include a counter that is provided in a channel array to detect the number of the particles that are selectively captured in the channel array.

For example, fourth counters 422, 424 may be provided in inlets and outlets of unit structures of fluidic channels.

Figure 19A:
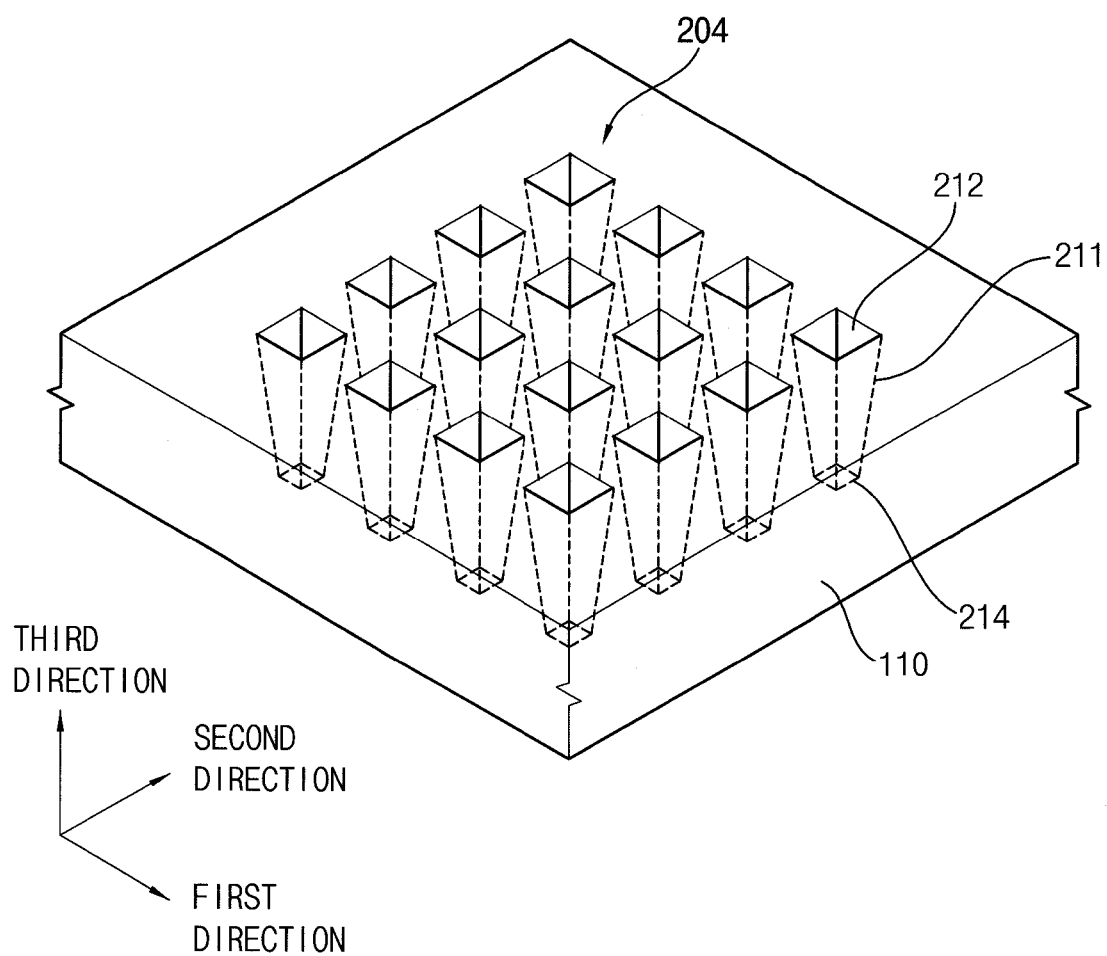
FIGS. 19A and 19B are perspective views illustrating a channel array of a particle processing device in accordance with another example embodiment.
Figure 19B:
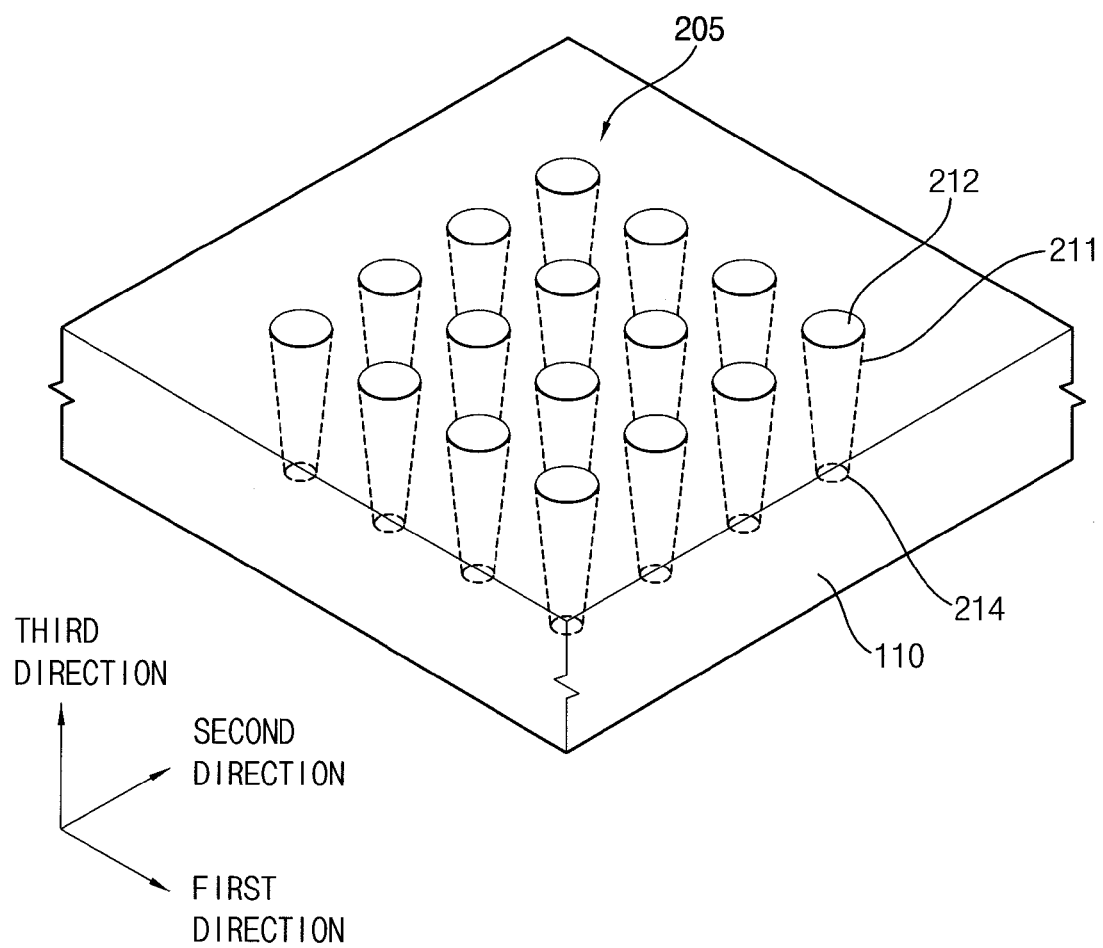

FIGS. 19A and 19B are perspective views illustrating a channel array of a particle processing device in accordance with another example embodiment.

Referring to FIGS. 19A and 19B, a particle processing device according to another example embodiment may include at least one channel array 204, 205 having fluidic channels 211 with 2-dimensional arrangement. The fluidic channels 211 may be arranged in an m×n matrix (where m and n are natural numbers) to form the channel array 204, 205.

In another example embodiment, the fluidic channels 211 of the channel array 204 may arranged repeatedly in a first and second directions perpendicular to each other.

The channel array 204 may be arranged in the chamber 110. The chamber 110 may have a polygonal or cylindrical shape. For example, the chamber 110 may extend in a third direction perpendicular to the first and second directions. Accordingly, the channel array 204 may be arranged on a plane defined by the first and second directions such that capturing structures of the channel array 204 may have the fluidic channels 211 with 2-dimensional arrangement. A fluid may flow through the channel array 204 in the third direction perpendicular to the plane of the channel array 204 in the chamber 110.

As illustrated in FIG. 19A, a fluidic channel 211 of the channel array 204 may a quadrangular pyramid shape. A first opening 212 of the fluidic channel 211 may have a first size and a second opening 214 of the fluidic channel 201 may have a second size smaller than the first size. Accordingly, a capturing region of a particle may be formed to have a changeable sectional shape between the first opening 212 and the second opening 214. The second size may be smaller than the minimum size of the particle that is deformed under a local pressure due to the physical characteristics of the particle such as deformability or stiffness.

As illustrated in FIG. 19B, a fluidic channel 211 of the channel array 205 may have a truncated cone shape. Accordingly, a capturing region of a particle may be formed to have a changeable sectional shape.

In addition, inner surfaces of the fluidic channels 211 of the channel array 204, 205 may be partially or entirely deformed to form the capturing region.

Hereinafter, a method of selectively capturing and collecting a particle in a fluid using the particle processing device in FIG. 1 will be explained.

FIGS. 20 to 25 are views illustrating a particle processing method in accordance with an example embodiment.

Figure 20:
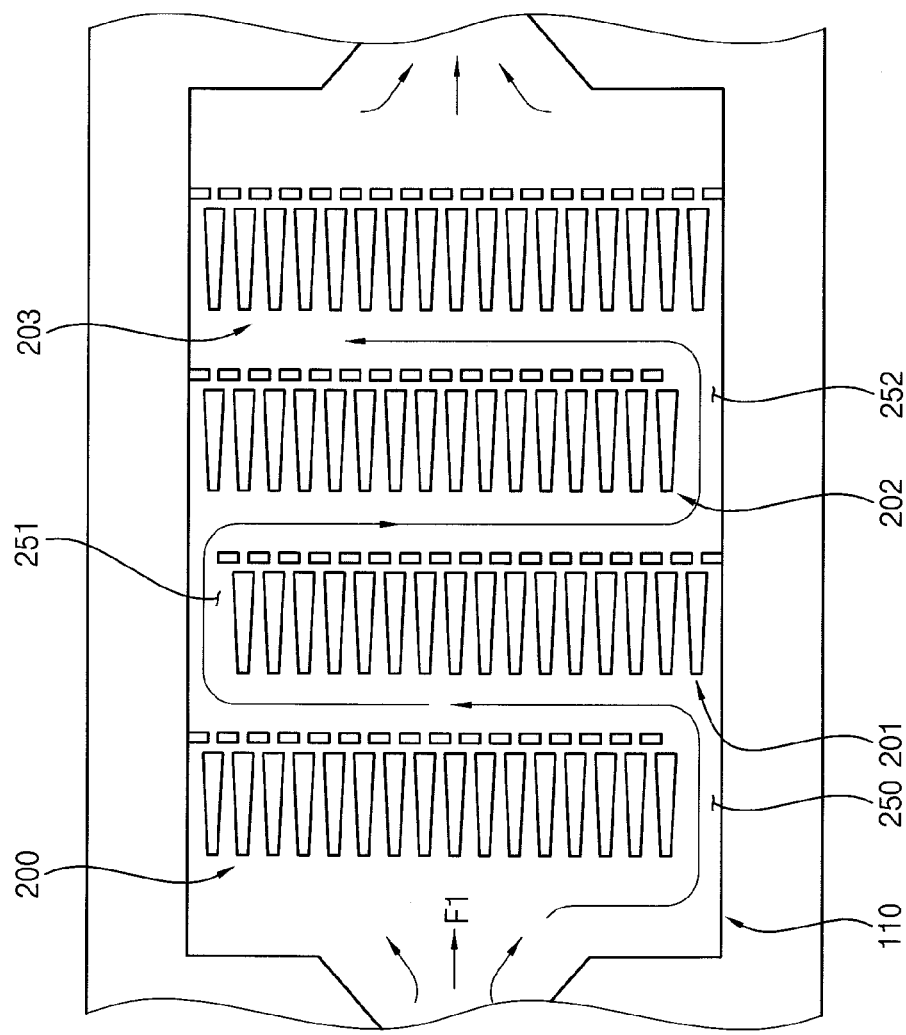

Referring to FIG. 20, a fluid having particles may flow from a first port 120 to a second port 130 through a chamber 110 by a hydrodynamic fluidic pressure.

In an example embodiment, when the fluid moves from the first port 120 to the second port 130 in the chamber 110, the fluid sequentially passes the first, second, third and fourth channel arrays 200, 201, 202, 203. In here, auxiliary pathes 250, 251, 252 may be provided in at least one of the channel arrays. The auxiliary pathes 250, 251, 252 may provide a space for an additional fluid flow to control the flow rate or flow direction of the fluid passing the channel arrays.

Figure 21:
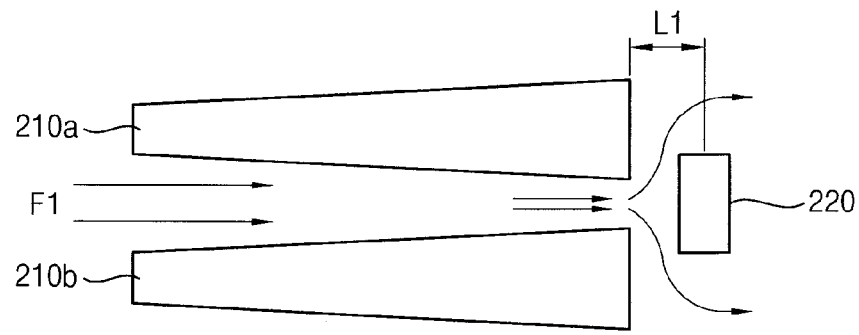

Referring to FIG. 21, the fluid may flow through unit structures of each of the channel arrays. In an example embodiment, when the fluid moves from the first port 120 to the second port 130 in a first flow direction (F1), the fluid may flow through a fluidic channel formed by an capturing structure of the unit structure and an auxiliary structure, and thus, pass through the channel array.

Figure 22A:
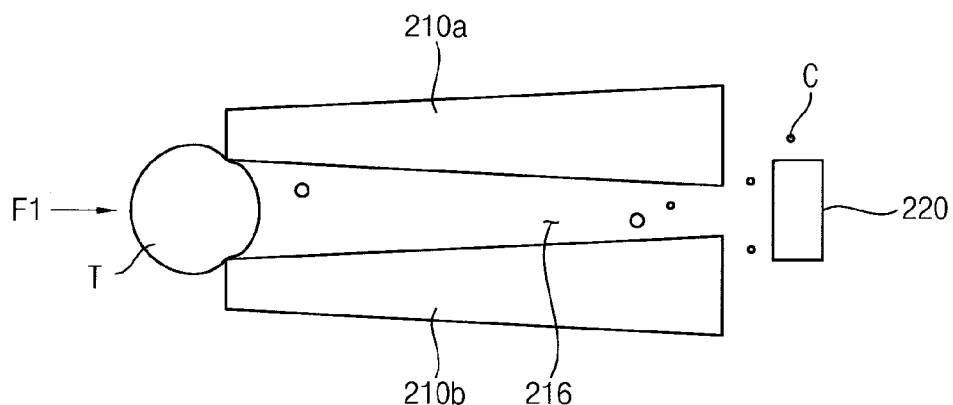
Figure 22B:
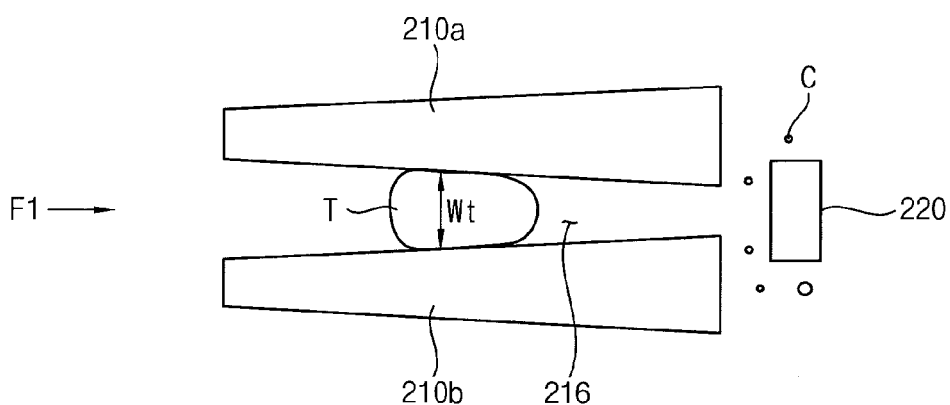

Referring to FIGS. 22A and 22B, in example embodiments, the target particle in the fluid may have a diameter (Wt) greater than those of other particles (C).

The other particles (C) except the target particle may pass through the fluidic channel of the capturing structure and the auxiliary structure and thus flow out of the channel array.

The target particle may have deformability under a local pressure in the channel array. The target particle having deformability may pass through a first opening of the capturing structure and enter the fluidic channel. A second opening of the capturing structure may have a diameter smaller than the minimum diameter of the target particle that is deformed by a local pressure.

Accordingly, the particle may be captured in a capturing region having a changeable sectional shape between the first opening and the second opening. Additionally, the capturing position of the target particle in the capturing region 216 may be determined according to the physical characteristics such as deformability or stiffness.

Figure 23:
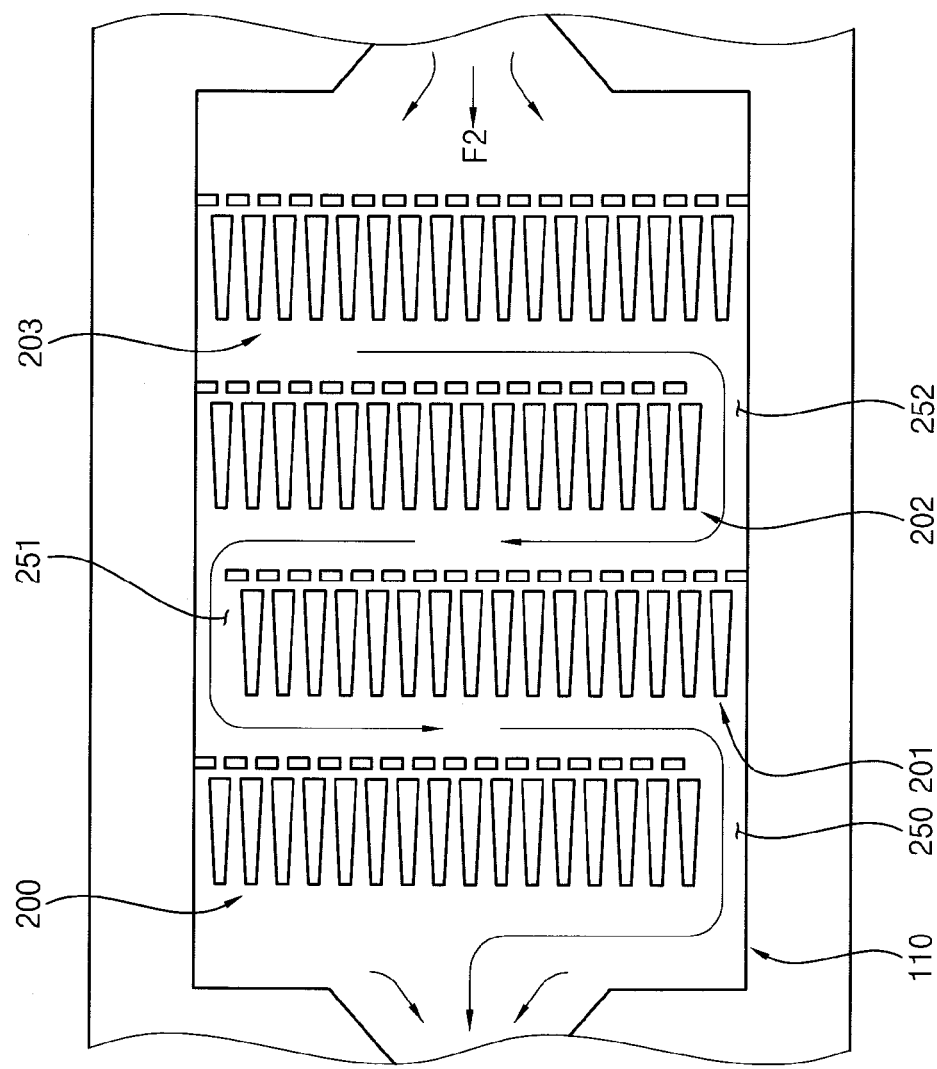

Referring to FIG. 23, in order to collect the captured particle, another fluid may flow from the second port to the first port 120 through the chamber 110 by a hydrodynamic fluidic pressure.

In an example embodiment, when the fluid moves from the second port 130 to the first port 120 in the chamber 110, the fluid sequentially passes the fourth, third, second and first channel arrays 203, 202, 201, 200. In here, the auxiliary pathes 252, 251, 250 may provide a space for an additional fluid flow to control the flow rate or flow direction of the fluid passing the channel arrays.

Figure 24:
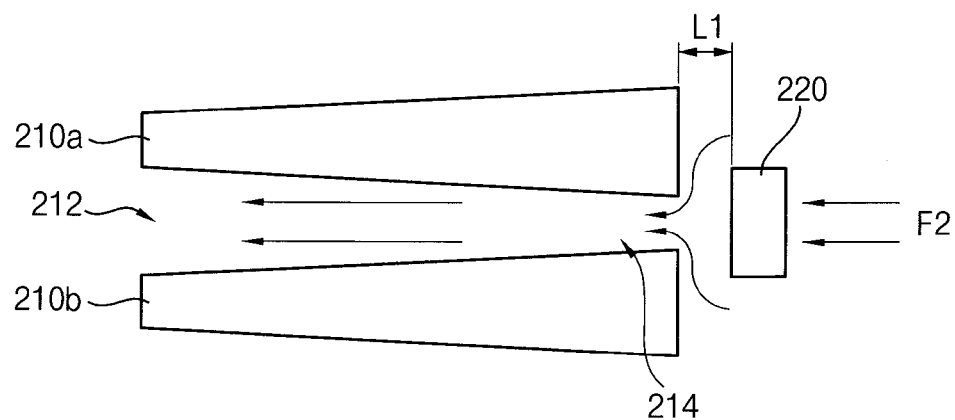

Referring to FIG. 24, the fluid may flow through the unit structures of each of the channel arrays.

In an example embodiment, when the fluid moves from the second port 130 to the first port 120 in a second flow direction (F2), the fluid may flow through the auxiliary structure of the unit structure and the fluidic channel of the capturing structure of the unit structure, and thus, pass through the channel array.

The auxiliary structure may be spaced apart from the second opening of the capturing structure by a first distance (L1). For example, the first distance (L1) may be smaller than the minimum diameter of the particle that is deformed. Accordingly, the auxiliary structure may prevent entering of undesired particles in the fluid into the fluidic channel of the capturing structure.

Figure 25:
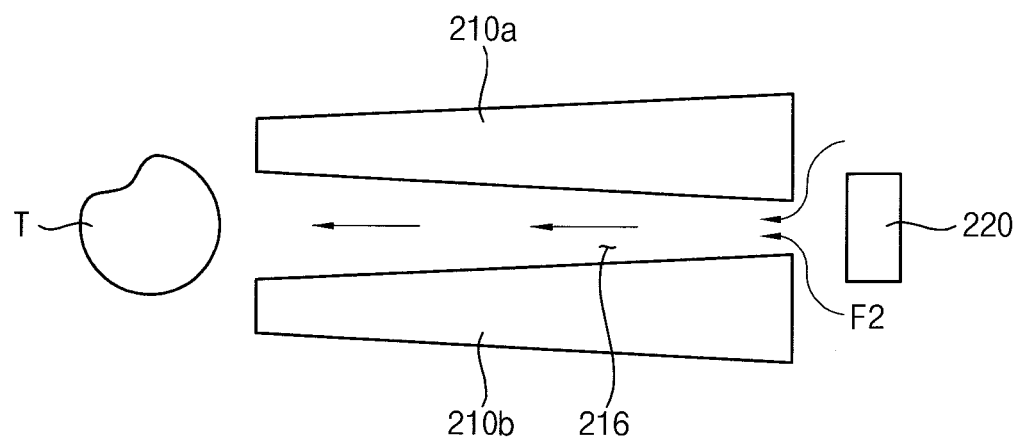

Referring to FIG. 25, when the fluid flows out of the fluidic channel of the capturing structure through the auxiliary structure, the target particle (T) remaining in the capturing region 216 of the capturing structure may come out through the first opening by the flowing of the fluid. Accordingly, the escaped particles may move into the first port 120 to be collected by the release element.

As mentioned above, the particle processing device may include at least one capturing structure formed in the fluidic chamber or a channel array including the capturing structure. The particle processing device may efficiently capture and collect particles by using bidirectional flow in the chamber and conduct real time quantitative analysis with a counter.

Further, in case that the particle in the fluid is biological organism, the particle processing device may efficiently capture and collect the particle in the fluid while maintaining its viability, and then, cultivate the particle.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A particle processing device, comprising:
a chamber connected to a first port and a second port opposite to each other to provide a space between the first and second ports through which a fluid having a particle flows;
at least one capturing structure provided in the chamber to form a fluidic channel, wherein the fluidic channel has a first opening and a second opening and a capturing region is formed between the first and second openings such that the capturing region has a changeable sectional shape for capturing the particle in the fluid flowing from the first port to the second port;
a first input/output portion including a first fluid supply element connected to the first port and a first fluid transfer element configured to transfer the fluid in a first direction from the first port to the second port through the fluidic channel;
a second input/output portion including a second fluid supply element connected to the second port and a second fluid transfer element configured to transfer a collection fluid in a reverse direction of the first direction from the second port to the first port through the fluidic channel;
wherein the capturing structure comprises a pair of first and second elongated channel patterns which are formed to extend between opposing upper and lower walls of the chamber to form the fluidic channel, the first and second channel patterns being elongated along an extending direction of the fluidic channel which is along the first direction through the fluidic channel;
wherein a distance between the opposing first and second channel patterns is decreased gradually along the extending direction of the fluidic channel to define the capturing region;
wherein when the first fluid transfer element transfers the fluid in the first direction from the first port to the second port, the first and second channel patterns are shaped to make contact with and capture a target particle in the capturing region between the first and second channel patterns;
wherein when the second fluid transfer element transfers a collecting fluid in the reverse direction of the first direction from the second port to the first port, the first and second channel patterns are formed such that the captured target particle escapes from the capturing region between the first and second channel patterns and moves to the first port;
a plurality of channel arrays provided in the chamber and capable of selectively capturing and collecting particles, each channel array including a plurality of the capturing structures;
an auxiliary structure disposed adjacent to the second opening of each capturing structure, the auxiliary structure being spaced apart from the second opening at a distance that is smaller than the minimum diameter of the fluidic channel, the auxiliary structure being disposed generally perpendicular to the fluidic channel, and the auxiliary structure having a shape that is different than the first and second channel patterns of each capturing structure;
the plurality of channel arrays being sequentially arranged in a direction from the first port to the second port; and
an auxiliary path arranged adjacent to each channel array such that each pair of auxiliary path and channel array are in a row perpendicular to the direction from the first port to the second port, the auxiliary paths being alternatingly arranged on opposite sides of the plurality of channel arrays in the direction from the first port to the second port, and the auxiliary paths being free of capturing structures.

2. The device of claim 1, wherein the first opening has a first size and the second opening has a second size smaller than the first size.

3. The device of claim 2, wherein the second size of the second opening is smaller than the minimum size of the particle that is deformed under a local pressure due to the physical characteristics of the particle such as deformability or stiffness.

4. The device of claim 1, wherein the width of at least one of the first and second channel patterns is gradually changed along the extending direction thereof to define the size of at least one of the first and second openings.

5. The device of claim 1, wherein at least one of the first and second channel patterns comprises a deformable polymer material membrane and a pressure line formed therein, and a predetermined pressure is applied into the pressure line to deform the deformable polymer material membrane to change the opening size of the fluidic channel.

6. The device of claim 5, wherein the pressure line is a pneumatic pressure line.

7. The device of claim 1, wherein any one of the upper and lower walls of the chamber comprises a deformable polymer material membrane and a pressure line formed therein, and a predetermined pressure is applied into the pressure line via pneumatic pressure such that the deformed wall and the first and second channel patterns form the fluidic channel.

8. The device of claim 5, wherein the deformable polymer material membrane forms an inner surface of the fluidic channel of the capturing structure.

9. The device of claim 1, wherein the auxiliary structure comprises at least one auxiliary structure pattern that is formed between opposing upper and lower sidewalls of the chamber.

10. The device of claim 9, wherein the auxiliary structure pattern comprises a deformable polymer material membrane and a pressure line formed therein, and a predetermined pressure is applied into the pressure line to deform the polymer material membrane to change the distance between the capturing structure and the auxiliary structure.

11. The device of claim 10, wherein the pressure line is a pneumatic pressure line.

12. The device of claim 1, wherein a biochemical material layer is formed on at least one of the capturing structure and the auxiliary structure or surface treatment is performed on the at least one of the capturing structure and the auxiliary structure to change surface characteristics, in order to increase or decrease the adhesive strength with the particle.

13. The device of claim 7, wherein the deformable polymer material membrane forms an inner surface of the fluidic channel of the capturing structure.

14. The device of claim 1, further comprising a counter which is provided in at least one of the first and second openings of the fluidic channel to detect the number of particles that are captured in the fluidic channel.

15. The device of claim 1, further comprising another auxiliary path which is arranged adjacent to each capturing structure in the chamber to control a flow rate of the fluid passing through the chamber.

* * * * *